United States Patent [19]
Poulin et al.

[11] Patent Number: 6,083,496
[45] Date of Patent: Jul. 4, 2000

[54] POLYAMINE TRANSPORT INHIBITORS

[75] Inventors: Richard Poulin; Marie Audette; René Charest-Gaudreault, all of Quebec, Canada

[73] Assignee: Universite Laval, Quebec, Canada

[21] Appl. No.: 08/735,130

[22] Filed: Oct. 22, 1996

[51] Int. Cl.[7] .................. A61K 31/74; A61K 31/785; A61K 31/765

[52] U.S. Cl. .................. 424/78.27; 424/78.37; 424/78.35

[58] Field of Search ............... 424/400, 78.27, 424/78.37, 78.35

[56] References Cited

PUBLICATIONS

Ask, et al., "Increased Survival of L1210 Leukemic Mice by Prevention of the Utilization of Extracellular Polyamines. Studies Using a Polyamine–Uptake Mutant, Antibiotics and a Polyamine–Deficient Diet," *Cancer Lett.* 66:29–34, 1992.

Azia, et al., "The Potential of a Novel Polyamine Transport Inhibitor in Cancer Chemotherapy," *J. Pharmacol. Exper. Ther.*, 278:185–192, 1996.

Azia, et al., "A Novel Polymeric Spermine Conjugate Inhibits Polyamine Transport in Pulmonary Artery Smooth Muscle Cells," *J. Pharmacol. Exp. Ther.*, 274:181–196, 1995.

Behr, et al., "Efficient Gene Transfer Into Mammalian Primary Endocrine Cells With Lipopolyamine–Coated DNA," *Proc. Natl. Acad. Sci, USA*, 86:6982–6986.

Behr, J.P., "Photohydrolysis of DNA by Polyaminobenzenediazonium Salts," *J. Chem. Soc., Chem. Commun.*, 101–103, 1989.

Bergeron, R.J., & J.R. Garlich, "Amines and Polyamines From Nitriles," *Communication*, 782–784.

Bergeron, et al., "Antiproliferative Properties of Polyamine Analogues: A Structure–Activity Study," *J. Med. Chem.*, 37:3464–3476, 1994.

Bergeron, et al., "The Role of Charge in Polyamine Analogue Recognition," *J. Med. Chem.*, 38:2278–2285, 1995.

Bergeron, et al., A Comparison of Structure–Activity Relationships Between Spermidine and Spermine Analogue Antineoplastics, *J. Med. Chem.*, 40:1475–1494, 1997.

Blais, et al., "Growth–Independent Induction of Spermidine Transport by IL–4 and IL–13 in ZR–75–1 Human Breast Cancer Cells," *Int. J. Cancer*, 67:532–538, 1996.

Byers, T.L., & A.E. Pegg, "Properties and Physiological Function of the Polyamine Transport System," *Am. J. Physiol.*, 257:C545–C553, 1989.

Byers, T.L., & A.E. Pegg, Regulation of Polyamine Transport in Chinese Hamster Ovary Cells, *J. Cell. Physiol.*, 143:460–467, 1990.

Byers, et al., "Expression of a Human Gene for Polyamine Transport in Chinese–Hamster Ovary Cells," *Biochem. J.*, 263:745–752, 1989.

(List continued on next page.)

*Primary Examiner*—Thurman K. Page
*Assistant Examiner*—Todd Ware
*Attorney, Agent, or Firm*—Arnold, White & Durkee

[57] ABSTRACT

Described herein are novel specific, pure competitive inhibitors of natural polyamine transport in mammalian cells. Despite their low molecular weight, the inhibitors of the present invention stay virtually impermeant to the cell and display minor non-specific effects while exhibiting a very high affinity for the carrier. More specifically described are synthetic derivatives of original polyamines, wherein the original polyamine is modified to comprise an amido group immediately linked to the polyamine backbone. A side chain may be anchored to the amido group and provide for the formation of dimeric synthetic derivatives or its labelling and subsequent usage as a marker for the polyamine transporter. The use of such novel inhibitors of polyamine transport to evaluate the antitumor efficacy of polyamine depletion strategies with minimal systemic cytotoxic effects or to control and treat disorders involving unrestrained cell proliferation and/or cell differentiation wherein polyamine transport is required as well as pharmaceutical composition thereof are also described.

23 Claims, 8 Drawing Sheets

OTHER PUBLICATIONS

Chaney, et al., "Tumor Selective Enhancement of Radioactivity Uptake in Mice Treated with α–Difluoromethylornithine Prior to Administration of $^{14}$C–Putrescine," *Life Sci.*, 32:1237–1241, 1983.

Duranton, et al., "Suppression of Preneoplastic Changes in the Intestine of Rats Fed Low Levels of Polyamines," *Cancer Res.*, 57:573–575, 1997.

Edwards, et al., "Polyamine Analogues With Antitumor Activity," *J. Med. Chem.*, 33:1369–1375, 1990.

Edwards, et al., "Synthesis and DNA–Binding Properties of Polyamine Analogues," *J. Med. Chem.*, 34:2414–2420, 1991.

Fleschow, et al., "Photoaffinity Labeling of a Cell Surface Polyamine Binding Protein," *J. Biol. Chemistry*, 270(48):28705–28711, 1995.

Gordonsmith, et al., "Structural Requirements of Compounds to Inhibit Pulmonary Diamine Accumulation," *Biochem. Pharmacol.*, 32:3701–3709, 1983.

Hayashi, et al., "Ornithine Decarboxylase Antizyme—A Novel Type of Regulatory Protein," *Sci.*, 21:27–30, 1996.

Hessels, et al., "Microbial Flora in the Gastrointestinal Tract Abolishes Cytostatic Effects of α–Difluoromethylornithine in vivo," *Int. J. Cancer*, 43:1155–1164, 1989.

Holley, et al., "Targeting of Tumor Cells and DNA by a Chlorambucil–Spermidine Conjugate," *Cancer Res.*, 52:4190–4195, 1992.

Hyvönen, et al., "Characterization of a COS Cell Line Deficient in Polyamine Transport," *Biochem Biophys. Acta*, 1221:279–285, 1994.

Kakimuma, et al., "Characterization of the Inducible Polyamine Transporter in Bovine Lymphocytes," *Eur. J. Biochem.*, 176:409–414, 1988.

Kallio, et al., "Transfer of Intestine–Derived Diamines Into Tumour Cells During Treatment of Ehrlich–Ascites–Carcinoma–Bearing Mice With Polyamine Anti–Metablites," *Biochem J.*, 218:641–644, 1984.

Kallio, et al., Modulation of the Tissue Disposition of Methylglyoxal Bis(Guanylhydrazone) in Mice By Polyamine Depletion and Polyamine Administration, *Cancer Res.*, 43:324–327, 1983.

Khan, et al., "Transport and Metabolism of Polyamines in Wild and Multidrug Resistant Human Leukemia (K 562) Cells," *Leuk. Res.*, 18:283–291, 1994.

Khan, et al., "Polyamine membrane Transport Regulation," *Cell Biol. Intl. Rep.*, 15:9–24, 1991.

Kumagai, et al., Characteristics of Spermidine Uptake By Isolated Rat Enterocytes, *Am. J. Physiol.*, 256:G905–G910, 1989.

Kumagai, J., & L.R. Johnson, "Characteristics of Putrescine Uptake in Isolated Rat Enterocytes," *Am. J. Physiol.*, 254:G81–G86, 1988.

Lakanen, et al., "α–Methyl Polyamines: Metabolically Stable Spermidine and Spermine Mimics Capable of Supporting Growth In Cells Depleted of Polyamines," *J. Med. Chem.*, 35:724–734, 1992.

Lessard, et al., "Hormonal and Feedback Regulation of Putrescine and Spermidine Transport in Human Breast Cancer Cells," *J. Biol. Chem.*, 270:1685–1694, 1995.

Li, et al., "Comparative Moleclar Field Analysis–Based Predictive Model of Structure–Function Relationships f Polyamine Transport Inhibitors in L1210 Cells," *Cancer Res.*, 57:234–239, 1997.

Minchin, et al., "Inhibition of Putrescine Uptake by Polypyridinium Quaternary Salts in B16 Melanoma Cells Treated with Difluoromethylornithine," *Biochem. J.*, 2262:391–395, 1989.

Mitchell, et al., "Feedback Repression of Polyamine Uptake Into Mammalian Cells Require Active Protein Synthesis," *Biochem. Biophys. Res. Commun.*, 186:81–88, 1992.

Mitchell, et al., "Feedback Repression of Polyamine Transport is Mediated By Antizyme in Mammalian Tissue–Culture Cells," *Biochem. J.*, 299:19–22, 1994.

Moulinoux, et al., Biological Significance of Circulating Polyamines in Oncology, *Cell. Mol. Biol.*, 37:773–783, 1991.

Nagarajan, et al., "Studies of Non–Metabolizable Polyamines That Support Growth of SV–3T3 Cells Depleted of Natural Polyamines By Exposure to α–Difluoromethylornithine," *Biochem. J.*, 254:373–378.

Nicolet, et al., "Putrescine and Spermidine Uptake is Regulated By Proliferation and Dexamethasone Treatment in AR4–2J Cells," *Int. J. Cancer*, 49:577–581, 1991.

Osborne, D.L., & E.R. Seidel, "Gastrointestinal Luminal Polyamines: Cellular Accumulation and Enterohepatic Circulation," *Am. J. Physiol.*, 258:G576–G584, 1990.

Pegg, A.E., "Polyamine Metabolism and Its Importance in Neoplastic Growth and as a Target for Chemotherapy," *Cancer Res.*, 48:759–774, 1988.

Pegg, et al., "Role of Unsaturated Derivatives of Spermidine As Substrates For Spermine Synthase and In Supporting Growth of SV–3T3 Cells," *Biochem J.*, 274:167–171, 1991.

Pegg, et al., "Use of Aminopropyltransferase Inhibitors and of Non–Metabolizable Analogs to Study Polyamine Regulation and Function," *Int. J. Biochem Cell. Biol.*, 27:425–442, 1995.

Persson, et al., "Curative Effect of DL–2–Difluoromethylornithine on Mice Bearing Mutant L1210 Leukemia Cells Deficient in Polyamine Uptake," *Cancer Res.*, 48:4807–4811, 1988.

Porter, et al., "Biological Properties of $N^4$–Spermidine Derivatives and Their Potential in Anticancer Therapy," *Cancer Res.*, 42:4072–4078, 1982.

Porter, et al., "Aliphatic Chain Length Specificity of the Polyamine Transport System in Ascites L1210 Leukemia Cells," *Cancer Res.*, 44:126–128, 1984.

Porter, et al., "Biological Properties of $N^4$ and $N^1, N^8$–Spermidine Derivatives in Cultured L1210 Leukemia Cells," *Cancer Res.*, 45:2050–2057, 1985.

Poulin, et al., "Inorganic Cation Dependence of Putrescine and Spermidine Transport in Human Breast Cancer Cells," *J. Biol. Chem.*, 270:1695–1704, 1995.

Quemener, et al., "Polyamine Deprivation: A New Tool in Cancer Treatment," *Anticancer Res.*, 14:443–448, 1994.

Rinehart, C.A., & K.Y. Chen, "Characterization of the Polyamine Transport System in Mouse Neuroblastoma Cells. Effects of Sodium and System A Amino Acids," *J. Biol. Chem.*, 259:4750–4756, 1984.

Seiler, N., & F. Dezeure, "Polyamine Transport in Mammalian Cells," *Int. J. Biochem.*, 22:211–218, 1990.

Seiler, et al., "Endogenous and Exogenous Polyamines in Support of Tumor Growth," *Cancer Res.*, 50:5077–5083, 1990.

Seppänen, et al., "Polyamine Deprivation–Induced Enhanced Uptake of Methylglyoxal bis(Guanylhydrazone) By Tumor Cells," *Biochem Biophys. Acta*, 674:169–177, 1981.

Shao, et al., "Isolation of a Polyamine Transport Deficient Cell Line From the Human Non–Small Cell Lung Carcinoma Line NCIh157," *J. Cell Physiol.,* 166:43–48, 1996.

Stark, et al., "Synthesis and Evaluation of Novel Spermidine Derivatives as Targeted Cancer Chemotherapeutic Agents," *J. Med. Chem.,* 35:4264–4269, 1992.

Torossian, et al., "Substrate Protection Against Inactivation of the Mammalian Polyamine Transport System By 1–Ethyl–3–(3–Dimethylaminopropyl)Carbodimide," *Biochem J.,* 319:21–26, 1996.

Volkow, et al., Labeled Putrescine as a Probe in Brain Tumors, *Science,* 221:673–675.

Huber et al., *J. Biol. Chem.,* 271(44), 27556–27563, 1996.

| R | NAME | $K_i (\mu M)$ |
|---|---|---|
| H | MESC | 33.6 ± 7.2 |
| —CH$_2$—C(=O)—NH$_2$ | MESC-iodoacetamide | 48.9 ± 9.1 |
| —CH$_2$—C(=O)—NH—CH$_2$CH$_2$—NH—C(=O)—(aromatic-SO$_3$/OH) | MESC-LY | 44.1 ± 8.8 |
| —CH$_2$—C(=O)—NH—(CH$_2$)$_n$—NH—C(=O)—(aryl-OH, N$_3$) | MESC-ASIB[a] | 18.3 ± 8.2 |

Fig. 5

POLYAMINE TRANSPORT INHIBITORS

FIELD OF THE INVENTION

The present invention relates to a novel class of competitive inhibitors of natural polyamine transport in mammalian cells. The present invention is more particularly directed to low molecular weight, high-affinity, specific, impermeant, pure antagonists of polyamine transport of a structure different to that of endogenous polyamines. The novel inhibitors of the present invention exhibit an effect on cultured tumor cells essentially cytostatic, with minor non-specific effects. The present invention is also directed to the use of such novel inhibitors of polyamine transport to evaluate the antitumor efficacy of polyamine depletion strategies with minimal systemic cytotoxic effects or to control and treat disorders involving unrestrained cell proliferation and/or cell differentiation wherein polyamine transport is required.

BACKGROUND OF THE INVENTION

Natural polyamines such as putrescine (1,4-butane-diamine), spermidine (N-[3-aminopropyl]-1,4-diaminobutane) and spermine (N,N'-bis-[3-aminopropyl]-1,4-butane-diamine) play essential roles in the control of macromolecular synthesis and growth processes in eukaryotic cells. Cells maintain appropriate polyamine concentrations principally by de novo synthesis from amino acids wherein ornithine decarboxylase catalyzes conversion of ornithine to putrescine, which is then converted to spermidine and spermine. Most tissues also possess a specific plasma membrane transport system allowing for utilization of plasma sources of polyamines.

Inhibitors of polyamine biosynthesis such as α-difluoromethylornithine (DFMO), which inhibits ornithine decarboxylase, cause an extensive depletion of polyamines followed by growth arrest in virtually all known mammalian cell types in vitro. Since tissues such as tumor cells and other transformed or rapidly proliferating cells exhibit a high demand for polyamines, these properties have encouraged an extensive assessment of such compounds for the treatment of proliferative diseases, including several types of tumors, in experimental models and in clinical trials. Unfortunately, the antitumor efficacy of such inhibitors in vivo has been disappointing. The failure of DFMO to halt tumor growth in animal models has been clearly correlated with the elevated polyamine transport activity found in transformed cells. Indeed, decontamination of the gastrointestinal tract, which is the main vector of circulating polyamines through bacterial microflora activity, along with a polyamine-free diet, markedly potentiate the in vivo efficacy of DFMO against tumor progression. Moreover, mutant mouse leukemia cells deficient in polyamine transport are much more susceptible than the parental strain to growth inhibition by DFMO treatment in host animals. Besides, growth inhibition associated with DFMO-induced polyamine depletion in ZR-75-1 human breast cancer cells can be completely reversed by concentrations of spermidine as low as 300 nM, i.e. such as those found in human plasma (Moulinoux, J. -P., Quemener, V., and Khan, N. A. 1991. *Cell. Mol. Biol.* 37: 773–783; Scalabrino, G. and Ferioli, M. E. 1981. *Adv. Cancer Res.* 36: 1–102; Bachrach, U. 1989, in *The Physiology of Polyamines* (Bachrach, U. and Heimer, Y. M., eds.) Vol. II, pp. 235–249, 2 vols, CRC Press, Boca Raton, Fla.). The striking efficiency of the transport system to salvage exogenous polyamines in DFMO-treated cells owes to its upregulation consecutive to polyamine depletion (Seiler, N. and Dezeure, F. 1990. *Int. J. Biochem.* 22: 211–218; Byers, T. L. and Pegg, A. E. 1990. *J. Cell. Physiol.* 143: 460–467; Lessard, M., Zhao, C., Singh, S. M. and Poulin, R. 1995. *J. Biol. Chem.* 270: 1685–1694; Kakinuma, Y., Hoshino, K., and Igarashi, K. 1988. *Eur. J. Biochem.* 176: 409–414). These data reinforce the view that cellular import of exogenous polyamines is the main factor limiting the efficacy of DFMO and other polyamine biosynthesis inhibitors as antitumor agents in vivo (Sarhan, S. Knödgen, B., and Seiler, N. 1989. *Anticancer Res.* 9: 215–224; Hessels, J., Kingma, A. W., Ferwerda, H., Keij, J., Van der Berg, G. A. and Muskiet, F. A. J. 1989. *Int. J. Cancer* 43: 115–1166; Ask, A., Persson, L. Heby, O. 1992. *Cancer Lett.* 66: 29–34; Seiler, N., Sarhan, S., Grauffel, C., Jones, R., Knödgen, B and Moulinoux, J. -P. 1990. *Cancer Res.* 50: 5077–5083; Persson, L., Holm, I., Ask, A. and Heby, O. 1988. *Cancer Res.* 48: 4807–4811).

Depletion of intracellular polyamines in tumor cells is thus a well-known strategy in anticancer therapies. However, it is now of common knowledge that depleting intracellular polyamines generally enhances polyamine uptake. To date, molecular information on the carrier molecules of the mammalian polyamine transport system is still unavailable. A few attempts have been made previously to design specific inhibitors of polyamine transport. Based on the finding that paraquat (4,4'-bipyridine) is a substrate of the putrescine transport system (Smith, L. L. and Wyatt, I. 1981. *Biochem. Pharmacol.* 30, 1053–1058; Rannels, D. E., Pegg, A. E., Clark, R. S. and Addison, J. L. 1985. *Am. J. Physiol.* 249, E506–E513), a series of polypyridinium salts, including compounds with a low $K_i$ against putrescine uptake and low acute toxicity for mammalian cells have been synthesized (Minchin, R. F., Martin, R. L., Summers, L. A. and Ilett, K. F. 1989. *Biochem. J.* 262, 391–395). However, it is unclear whether such compounds can efficiently inhibit polyamine transport or are accumulated intracellularly. A number of polyamine analogs are effective competitors of polyamine uptake while being themselves substrates for transport (Seiler, N. and Dezeure, F. 1990. *Int. J. Biochem.* 22: 211–218; Pegg, A. E., Poulin, R. and Coward, J. K. 1995. *Int. J. Biochem. Cell. Biol.* 27: 425–442; Bergeron, R. J., and Seligsohn, H. W. (1986) *Bioinorg. Chem.* 14: 345–355; Porter, C. W., Bergeron, R. J. and Stolowich, N. J. 1982. *Cancer Res.* 42: 4072–4078; Porter, C. W., Bergeron, R. J. and Stolowich, N. J. 1982. *Cancer Res.* 42: 4072–4078; Porter, C. W. and Bergeron, R. J. 1983. *Science* 219: 1083–1085). These analogs share many structural features of the natural polyamines and can be used as substitutes or have cytotoxic effects in mammalian cells alone or in combination with DFMO (Marton, L. J. and Pegg, A. E. 1995. *Ann. Rev. Pharmacol. Toxicol.* 35: 55–91; Pegg, A. E., Poulin, R. and Coward, J. K. 1995. *Int. J. Biochem. Cell. Biol.* 27: 425–442; Bergeron, R. J. and Seligsohn, H. W. 1986. *Bioinorg. Chem.* 14: 345–355; Porter, C. W., Cavanaugh, P. F., Jr., Stolowich, N., Ganis, B., Kelly, E., and Bergeron, R. J. 1985. *Cancer Res.* 45: 2050–2057; Porter, C. W., Bergeron, R. J. and Stolowich, N. J. 1982. *Cancer Res.* 42: 4072–4078; Porter, C. W., Basu, H. S., Feuerstein, B. G., Deen, D. F., Lubich, W. P., Bergeron, R. J., Samejima, K., and Marton, L. J. 1989. *Cancer Res.* 49: 5591–5597; Pegg, A. E., Wechter, R., Pakala, R. and Bergeron, R. J. 1989. *J. Biol. Chem.* 264: 11744–11749; Pegg, A. E., Nagarajan, S., Naficy, S. and Ganem, B. 1991. *Biochem. J.* 274: 167–171; Porter, C. W., Ganis, B., Libby, P. R. and Bergeron, R. J. 1991 *Cancer Res.* 51: 3715–3720).

More recently, a high-molecular weight (Mr=25 Kd) spermine polymer has been described by Aziz et al. in U.S. Pat. No. 5,456,908, as a competitive inhibitor of polyamine transport, with a $K_i$ in the $10^{-6}M$ range. In this patent document are disclosed two novel classes of polyamine transport inhibitors of high molecular weight, namely polymeric conjugates of normally transported substances (TS) of the structure $(TS)_n$, or conjugates of a polyamine and a protein or polypeptide (P) linked by known coupling agents and represented by (TS)-(P), wherein the repeating units of the polymer comprise the targeted polyamine. It is predictable that the inhibitors of Aziz et al. would be difficult to eliminate in vivo due to their high molecular weight and the high positive charge of the polymers, notwithstanding the risk of immunogenicity inherent to such high molecular weight inhibitors. The length of the polymers of Aziz et al. as well as their charge would cause their adsorption to the cellular surface, which bears negative charges due to the presence of glycoproteins, e.g. sialic acid. Poly-L-lysine, a commercially used compound analogous to high molecular weight polymers of polyamines by its positive charges, is known to promote a strong electrostatic interaction between the cell and its substrate, as is the induction of positive charges by gamma irradiation of synthetic polymers used to produce dishes for tissue culture. The polyamine transport inhibitors of Aziz et al. present the additional drawback of being highly cytotoxic. It is noteworthy that their spermine polymer is effective in decreasing contents of polyamines in cells even when not used in combination with DFMO and at concentrations much higher than those required to block polyamine uptake, which indicates an inherent high toxicity of the compound toward the cell by a mechanism independent of polyamine transport per se. The cytotoxicity of the spermidine polymer of Aziz et al. is most problably explained by a non-specific effect on cellular physiology such as on the cellular membrane. Although the authors pretend to demonstrate the specific action of their polymers with the fact that exogenous spermidine reverses the induced cytotoxicity, it is highly likely that competition between spermidine and the polymers or electrostatic interaction with the negatively-charged sites on the cellular membrane is responsible for this effect. The results obtained by Aziz et al. indicate that at least part of the effect observed with high molecular weight polymers is non-specific (Aziz, S. M., Tofiq, S. F., Gosland, M. P., Olson, J. W. and Gillespie, M. N. 1995. *J. Pharmacol. Exp. Ther.* 274, 181–196). The usefulness of this spermine polymer for specifically blocking polyamine accumulation is therefore uncertain in view of its marked cytotoxicity.

Cysteamine and aliphatic monoamines of similar chain length such as n-butylamine and n-pentylamine have a low but significant ability to antagonize putrescine uptake (Gordonsmith, R. H., Brooke-Taylor, S., Smith, L. L. and Cohen, G. M. 1983. *Biochem. Pharmacol.* 32, 431–437), although the mode of inhibition of these compounds has not been reported. The only other polyamine-like structure known to interact non-competitively with the polyamine transport system is pentamidine, an aromatic diamidine (Jones, H. E., Blundell, G. K., Wyatt, I., John, R. A., Farr, S. J. and Richards, R. J. 1992. *Biochem. Pharmacol.* 43, 431–437), but the structural basis of its inhibitory activity is not yet clear.

It follows that there still exists a need for effective polyamine transport inhibitors which, while inhibiting the transport of polyamines, will not be internalized by the transport system and will not be toxic to the cell. The availability of low molecular weight inhibitors of polyamine transport would provide for the possibility of better renal elimination, as well as lower risks of being immunogenic. The availability of high-affinity, specific, but impermeant antagonists of polyamine transport would also allow to evaluate the antitumor efficacy of polyamine depletion strategies in vivo with minimal systemic cytotoxic effects.

STATEMENT OF THE INVENTION

In accordance with the present invention, there is now provided polyamine transport inhibitors having a low molecular weight, less susceptible to immunogenicity and to non-specific interactions with the cellular membrane. These inhibitors have high affinity, are specific, impermeant, pure antagonists of polyamine transport in mammalian cells while exhibiting minimal cytotoxic effects.

There is thus provided in accordance with the present invention synthetic derivatives of original polyamines, wherein the original polyamine is modified to comprise an amido group immediately linked to a carbon atom of said original polyamine, said synthetic derivatives inhibiting the cellular uptake of natural polyamines by specifically binding cellular transporters for said natural polyamines. Surprisingly, the immediate vicinity of the amido group to the backbone of the original polyamine preserves the specificity of the derivative towards the transporter while conferring thereto an impermeant character, providing a true antagonist. In a particularly preferred embodiment, the amido group is located between two internal nitrogen atoms of the original polyamine. In a most preferred embodiment, the synthetic derivative comprises a dimer wherein monomers of said dimer are linked together by a spacer side chain anchored to the amido group of each monomer.

Although natural polyamines such as putrescine, spermine and spermidine can be used as the original polyamine, other non natural polyamines can be used as a starting material for the making of synthetic derivatives as taught by the present invention.

Accordingly, a synthetic derivative comprising the following general formula

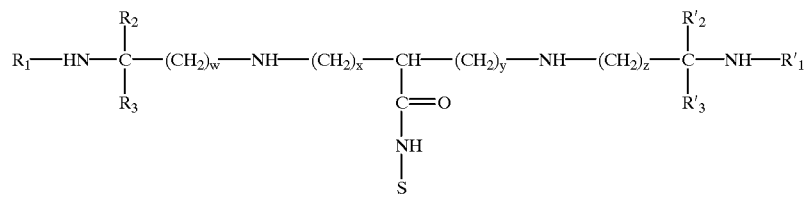

has been obtained, in which $R_1$ and $R'_1$ independently represent a hydrogen atom or an alkyl group having 1 to 2 carbon atoms, $R_2$, $R'_2$, $R_3$ and $R'_3$ independently represent a hydrogen atom or a methyl group, w and z independently represent an integer of 2 or 3, x represents an integrer from 0 to n, n represents an integrer from 3 to 6, the sum of x and y equals n, and S represents a hydrogen atom or a molecule which cannot be captured by said natural polyamine transporter. The side chain S may be labelled and be used as a marker for a polyamine transporter. Furthermore, the side chain S can be varied to increase the affinity of the derivative for the transporter. The side chain S may also become a spacer molecule useful in the formation of a dimer. This spacer side chain comprises a linear hydrocarbon-containing backbone of 3 to 8 atoms. The backbone may comprise sulfur, oxygen, or nitrogen atoms.

In a specific embodiment, the original polyamine is spermine. Three derivatives have been obtained therefrom: N-(2-mercaptoethyl)spermine-5-carboxamide (MESC), the disulfide form thereof, namely 2,2'-dithiobis(N-ethyl-spermine-5-carboxamide) (DESC), and N-[2,2'-Dithio(Ethyl, 1'-Aminoethyl)]spermine-5-carboxamide (DEASC).

It is another object of the invention to provide the use of all the above synthetic derivatives for inhibiting the activity of a natural polyamine transporter, comprising the step of contacting said transporter with an inhibitory effective amount of said synthetic derivative. This inhibition results in the control or the treatment of disorders involving unrestrained cell proliferation and/or differentiation where control of polyamine transport is required, when used in combination with an inhibitor of polyamine synthesis such as DFMO.

It is further another object of the invention to provide a use of the non-dimeric derivatives as a marker for a polyamine transporter, which comprises the steps of labelling said synthetic derivative, binding to said transporter said labelled synthetic derivative and detecting said bound labelled marker as an indication of the presence of said polyamine transporter. The above sequence of steps results in the diagnosis of a disorder involving unrestrained cell proliferation and/or differentiation where control of polyamine transport is required.

It is also another object of the invention to provide a pharmaceutical composition for treating disorders wherein control of polyamine transport is required, comprising anyone of all the above derivatives in adjunction with an acceptable pharmaceutical carrier. Preferably, this composition also comprises an inhibitor of polyamine synthesis, such as DFMO.

SUMMARY OF THE INVENTION

The applicants have unexpectedly discovered that the presence of a lateral amido group immediately linked to a carbon atom of the polyamine backbone of a synthetic derivative of an original polyamine confers impermeant properties to the so derived synthetic polyamine against the mammalian cell. It follows that the synthetic polyamine derivatives of the present invention, by exhibiting high affinity for diamine and polyamine transport systems, block the transport of natural polyamines by competing therewith, while in the same time acting as poor substrate for intracellular uptake. The affinity of the polyamine derivative for the transporter system is further enhanced by increasing the length of a side chain anchored to the amido group of the derivative. The best affinity is achieved by dimerizing the polyamine derivative with the aid of a spacer molecule anchored at both ends to the amido group of each monomer. The flexibility of the chemical structure of the inhibitors of the present invention permits better optimization of the activity and affinity than a simple polymeric structure such as $(TS)_n$. For example, modifications to the polyamine backbone as taught by the present invention, such as methylation of C1 to C12, lowers the possibility of oxidation of the primary amines by the serum amine oxidase, which is present in mammalian sera. Additional modifications including adjunction to the lateral chain of alkylating groups that irreversibly modify residues that are essential to the activity of the polyamine transporter, such as carboxylic moieties of the carrier protein, are also contemplated in the present invention (Torossian, K., Audette, M., and Poulin, R. 1996. *Biochem. J.* 319: 21–26). The inhibitory action of the derivatives of the present invention is thus enhanced. By diminishing the amount of active transporters, additional modifications to the side chain that can be of potential therapeutic interest include the incorporation of reactive groups to the side chain that would allow the covalent modification of residues in the polyamine transporter by the principle of affinity labelling, and its subsequent irreversible inactivation.

This finding clearly demonstrates that modification of the chemical structure of the lateral chain optimizes the affinity of the polyamine derivative without augmenting to a great extent the molecular weight thereof. This markedly contrasts with the teachings of Aziz et al., who make use of high molecular weight polymers. Moreover, the mode of action of the inhibitors herein proposed, clearly different to that of Aziz et al. which relies upon their inherent cytotoxicity, is a competitive inhibition of the polyamine uptake.

Other objects, advantages and features of the present invention will become more apparent upon reading of the following non restrictive description of preferred embodiments thereof, given by way of examples only and with reference to the accompanying drawings.

BRIEF DESCRIPTION OF THE DRAWINGS

In the appended drawings:

FIG. 5 illustrates graphically the structure of MESC thioether derivatives and their $K_i$ values with respect to spermidine uptake in CHO-K1 cells. The various conjugates were prepared from MESC as described supra, and structure and name of the substituents are given in the first two columns from the left, wherein R corresponds to the group attached to sulfur in MESC (structure VII, FIG. 1). The rate of spermidine uptake was determined in CHO-K1 cells in the presence of increasing concentrations of the various MESC derivatives, using 1 μM [$^3$H]spermidine as substrate. $K_i$ values are given as the means±SD of triplicate determinations from 2 to 3 experiments;

DETAILED DESCRIPTION OF THE INVENTION

MATERIALS AND METHODS

Figure 1:
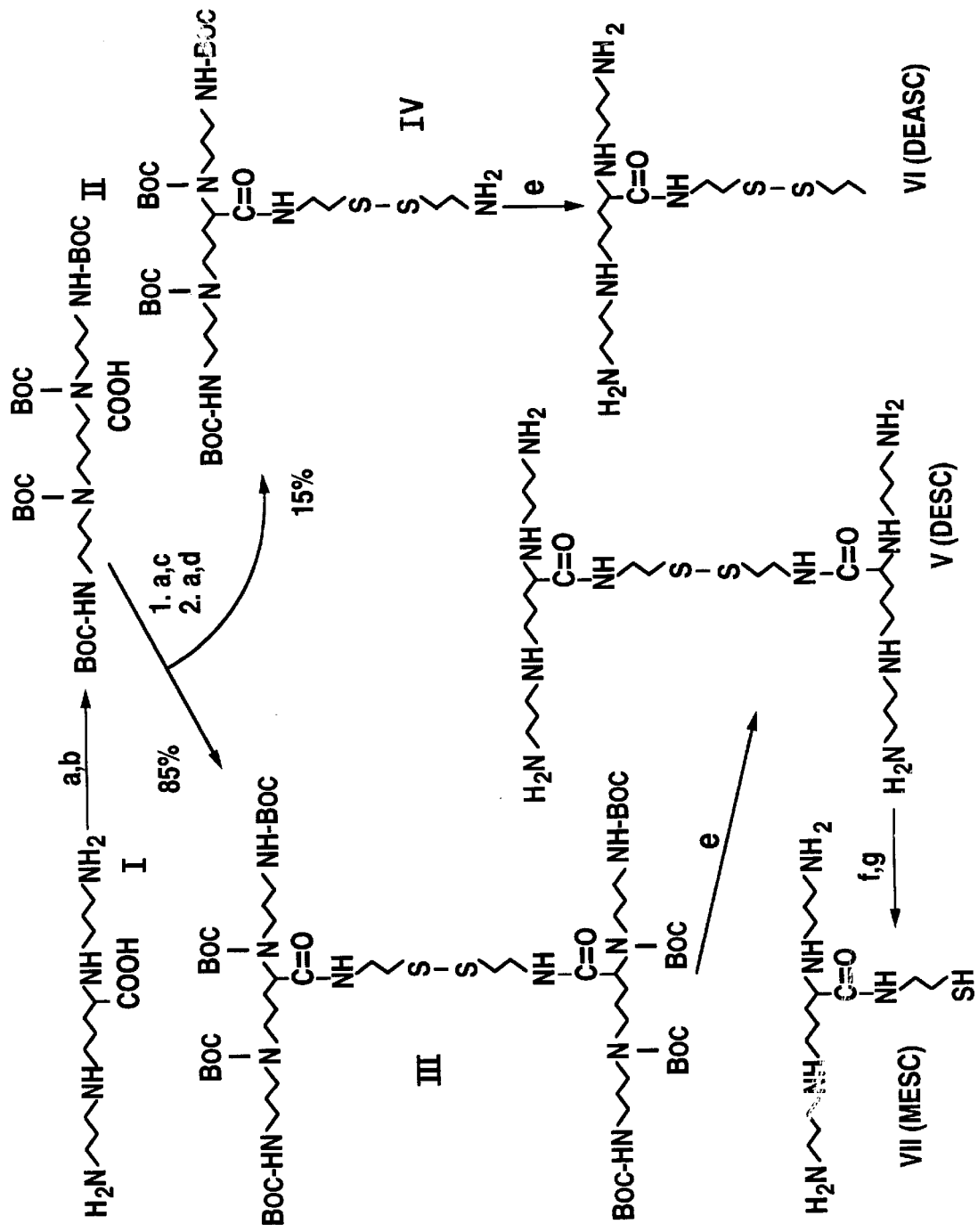
FIG. 1 illustrates details of the synthesis of the compounds of the present invention, wherein a=triethylamine; b=di-tert-butyl dicarbonate; c=cyanuric chloride; d=cystamine dihydrochloride; e=3 N HCl: f=dithiothreitol; g=50 mM sodium phosphate in aqueous solution (pH=8.0); and wherein compound I is 5-carboxyspermine; compound II is tetra-Boc-5-carboxyspermine; compound III is 2,2'-dithiobis[N-ethyl-($N^1$, $N^4$, $N^8$, $N^{12}$)-tetra-Boc-spermine-5-carboxamide; compound IV is N-[2,2'-dithio(ethyl, 1'-aminoethyl)]-$N^1$, $N^4$, $N^8$, $N^{12}$-tetra-Boc-spermine-5-carboxamide; compound V is 2,2'-dithiobis(N-ethyl-spermine-5-carboxamide) octahydrochloride; compound VI is N-[2,2'-dithio(ethyl, 1'-aminoethyl)]-spermine-5-carboxamide (DEASC) and compound VII is N-(2-mercaptoethyl) spermine 5-carboxamide (MESC) tetrahydrochloride.

Sym-norspermidine, ornithine dihydrochloride and other reagents for organic syntheses were purchased from Aldrich (Milwaukee, Wis.) and Sigma (St. Louis, Mo.). Reversed phase silica gel liquid chromatography was performed with a Lichroprep™ RP-18 $C_{18}$ silica gel column (40–63 μm; BDH, St. Laurent, Qc., Canada) using a gradient of $CH_3CN:MeOH:H_2O$ (25:35:40 to 50:30:20) as eluent. Homogeneity of synthetic products was assessed by thin-layer chromatography performed on 0.20 mm $F_{254}$ silica gel 60 plates or 0.25 mm $F_{245}S$ RP-18 reversed phase silica gel plates (E. Merck, Darmstadt, Germany). FIR spectra were obtained on a Perkin-Elmer 1600 spectrophotometer (FTIR series) and were expressed in $cm^{-1}$. $^1H$ and $^{13}C$ NMR spectra were recorded with a Bruker AC/F 300 (300 MHz); $^{13}C$ were recorded at 75.47 MHz. Chemical shifts (δ, in ppm) were referenced to $CDCl_3$ (7.26 ppm for $^1H$ and 77.00 ppm for $^{13}C$). Mass spectra (MS) were recorded at the Mass Spectrometry Regional Center (University of Montreal, Montreal, Qc., Canada) by fast atomic bombardment mass spectrometry (FABMS) or liquid secondary ion mass spectrometry (LSIMS), using a VG AutoSpecQ™ and a Kratos MS50 TCTA, respectively.

[2,3-$^3$H(N)]putrescine dihydrochloride (4.1×10$^4$ Ci/mol) and [1,8-$^3$H(N)]spermidine trihydrochloride (1.5×10$^4$ Ci/mol) were obtained from Dupont-New England Nuclear (Lachine, Qc., Canada). [5,8-$^{14}$C]spermine tetrahydrochloride (108 Ci/mol) was purchased from Amersham (Arlington Heights, Ill.). DFMO was generously provided by the Marion Merrell Dow Research Institute (Cincinnati, Ohio). Fetal bovine serum (FBS) and Cosmic™ calf serum were from Hyclone (Logan, Utah). The heterobifunctional reagent 1-(p-azidosalicylamido)-4-(iodoacetamido)butane (ASIB) was obtained from Pierce (Rockford, Ill.). Lucifer Yellow (LY) iodoacetamide was purchased from Molecular Probes (Eugene, Oreg.). Putrescine dihydrochloride, spermidine trihydrochloride, spermine tetrahydrochloride, iodoacetamide, 5,5'-dithio(2-nitrobenzoic acid) and 3,5-diaminobenzoic acid as well as tissue culture reagents were purchased from Sigma. Ortho-phthaldialdehyde was purchased from Fluka (Ronkonkoma, N.Y.) and other reagents for high-performance liquid chromatography (HPLC) were from Fisher Scientific (Montreal, Qc., Canada) or Aldrich (Milwaukee, Wis.).

Synthesis of 5-carboxyspermine (compound I)—Unless otherwise indicated, reactions were performed at room temperature. Compound I of FIG. 1, namely 5-carboxyspermine, was synthesized using a known scheme (Behr, J. P. 1989. *J. Chem. Soc., Chem. Commun.* 101–103). Briefly, to a stirred solution of 10.0 g (59.3 mmol) of ornithine hydrochloride dissolved in 250 ml MeOH were added 18.0 g (197 mmol) of tetramethylammonium hydroxide. After dissolution of ornithine salt, MeOH was evaporated, the mixture was then dissolved in 350 mL of dry dimethylformamide (HPLC grade; Aldrich, Milwaukee, Wis.) and the residual ammonium salt was filtrated, yielding ornithine as its free base. Following the addition of acrylonitrile (2.2 equivalents, 130.9 mmol), the mixture was stirred for 16 hours in the dark to give 10.5 g (yield=74%) of crude $N^α,N^δ$-diethylcyanide ornithine, which was subsequently used without further purification. White solid; IR (film) v cm$^{-1}$ 3372 (OH, acid), 2247 (CN); $^1$H NMR δ (CDCl$_3$, 300 MHz) 1.48 (m, 4H, CH$_2$CH$_2$CHCOOH), 2.63 (m, 6H, 3×CH$_2$n), 2.86 (2xt, J$_1$=5.9 and J$_2$=2.7 Hz, 4H, 2×CH$_2$CN), 3.07 (t, J=7.2 Hz, 1H, CHCOOH). To obtain 5-carboxyspermine, KOH (2.7g, 48.0 mmol) was dissolved with vigorous stirring in 8 ml of 95% (v/v) EtOH and 10.5 g (44.1 mmol) of N$^α$,N$^δ$-diethylcyanide ornithine were then added. The resulting mixture was placed under H$_2$ at 40 psi in a Burgess-Parr hydrogenator, using 2.09 g (24.4 mmol) of Raney nickel as catalyst (Behr, J. P. 1989. *J. chem. Soc., Chem. Commun.* 101–103; Bergeron, R. J. and Garlich, J. R. 1984. *Synthesis;* 782–784). After 22 hours, Raney nickel was removed by filtration, and the solvent evaporated in vacuo, yielding 16.07 g of the crude 5-carboxyspermine potassium salt. Yellow oil; IR (film) v cm$^{-1}$ 3363 (OH, acid), 2937 (NH$_2$), no cyanide band; $^1$H NMR δ (CDCl$_3$, 300 MHz) 1.53 (m, 2H, CH$_2$CHCOOH), 1.65 (m, 6H, CH$_2$CH$_2$CH$_2$), 2.51 (m, 4H, 2×CH$_2$NH$_2$), 2.65 (m, 6H, CH$_2$NH), 3.09 (t, J=5.7 Hz, 1H, CHCOOH).

Synthesis of 2,2'-Dithiobis(N-Ethyl-Spermine-5-Carboxamide) (DESC) and N-[2,2'-Dithio(Ethyl,1'-Aminoethyl)] spermine-5-Carboxamide (DEASC)—Amine protection of 5-carboxyspermine by tert-butyl carbonyl (Boc) groups was performed as described (Ponnusamy, E., Fotadar. U., Spisni, A. and Fiat, D. 1986. *Synthesis:* 48–49). To 16.0 g (65.0 mmol) of crude 5-carboxyspermine potassium salt dissolved in 1.5 L MeOH were added 9.64 ml of 10% (v/v) triethylamine and 54.3 g (4.4 equivalents, 286 mmol) of di-tert-butyl dicarbonate. After stirring for 24 hours, solvent was evaporated, 100–150 ml H$_2$O were added and the resulting mixture was chilled at 0° C. After adjusting pH at 2.2 with 2 N HCl, the Boc-product was extracted with ethyl acetate, dried over anhydrous MgSO$_4$ and purified by C$_{18}$ reversed phase silica gel chromatography, yielding 3.3 g of pure tetra-Boc-5-carboxyspermine (Compound II, FIG. 1). Light yellow solid; IR (film) v cm$^{-1}$ 3356 (OH, acid), 1682 (C=O, amide); $^1$H NMR δ (CDCl$_3$, 300 MHz) 1.32 (2×s, 36 H, (CH$_3$)$_3$C from Boc-N), 1.90–1.40 (m, 8H, CH$_2$CH$_2$N), 3.20–2.90 (m, 10H, CH$_2$N); M (for C$_{31}$H$_{58}$O$_{10}$N$_4$)=646.41; m/z (LSIMS)=647.42 [(M+1)$^+$]. Coupling of tetra-Boc-5-carboxyspermine (compound II) to cystamine was then performed in two steps based on the method of Venkataraman (Venkataraman, K. 1979. *Tetrahedr. Lett.* 32, 3037). To a solution of 1.15 g (1.78 mmol) of compound II in 20 ml dry acetone was added 0.27 mL (1.1 eq, 1.96 mmol) of triethylamine (freshly distilled on KOH) and 361 mg (1.1 eq, 1.96 mmol) of cyanuric chloride and the reaction mixture stirred overnight under N$_2$ to form the corresponding acid chloride. Cystamine dihydrochloride (241 mg; 1.07 mmol) was then suspended in dry triethylamine and added to the acid chloride form of compound II, with the resulting triethylamine concentration being at ≧4-fold excess relative to the latter. After stirring for 12 hours, the residual triazine oxide was filtrated, acetone was evaporated and the product extracted with CHCl$_3$, dried over anhydrous MgSO$_4$ and evaporation in vacuo. The crude compound was then purified by reversed phase C$_{18}$ column chromatography, yielding 0.682 g of 2,2'-dithiobis[N-ethyl-(N$^1$,N$^4$N$^8$,N$^{12}$)-tetra-Boc-spermine-5-carboxamide] (compound III, FIG. 1) and 0.124 g of N-[2,2'-dithio(ethyl, 1'-aminoethyl)]-N$^1$,N$^4$,N$^8$,N$^{12}$-tetra-Boc-spermine-5-carboxamide (compound IV, FIG. 1). (m) Yellow oil; IR (film) v cm$^{-1}$ 1693 (C=O, amide); $^1$H NMR δ (CDCl$^3$, 300 MHz) 1.38 (s, 36H, (CH$_3$)$_3$C), 1.59 (m, 8H, CH$_2$CH$_2$CH$_2$), 2.53 (t, J=5.7 Hz, 1H, CONHCH$_2$), 2.78 (t, J=6.1 Hz, 2H, CH$_2$S), 3.11 (m, 10H, CH$_2$NH), 3.51 (m, 2H, NCH$_2$CH$_2$S); M (for C$_{88}$H$_{124}$O$_{18}$N$_{10}$S$_2$)=1408.85; m/z (FABMS)=1409.9 [(M+1)$^+$].

Compound III (215 mg in MeOH) was then deprotected by addition of 1 ml of 3 N HCl, bringing the pH from 6.0 to ~0.5 After stirring vigorously for 15 hours, the solvent was dried out in vacuo and the resulting compound purified by cation exchange chromatography with a Dowex 50W-X4 column (dry mesh: 100–200; Sigma) pre-equilibrated with H$_2$O and successively washed with H$_2$O, 1 N HCl, 2 N HCl, 4 N HCl and 6N HCl. Ninhydrin-positive fractions eluted with 6 N HCl were pooled and evaporated in vacuo, yielding 96 mg of pure 2,2'-dithiobis(N-ethyl-spermine-5-carboxamide)-octahydrochloride (DESC, Compound V, FIG. 1). White solid; mp 75–78° C.; bp 118° C. $^1$H NMR δ (CDCl$_3$, 300 MHz), 1.62 (m, 2H, CH$_2$CHCONH), 1.97–1.80 (m, 6H, CH$_2$CH$_2$CH$_2$), 2.74 (t, J=6.2 Hz, 2H, CH$_2$S), 2.92 (m, 10H, CH$_2$NH), 3.46 (dt, J=7.1 Hz, 2H, CH$_2$CH$_2$S), 3.84 (t, J=7.0 Hz, 1H, CHCONH); M (for C$_{26}$H$_{60}$O$_2$N$_{10}$S$_2$)=608.96; m/z (FABMS)=609.4 (M$^+$).

Compound IV was similarly deprotected to yield N-[2, 2'-dithio(ethyl,1'-aminoethyl)]spermine-5-carboxamide (DEASC, Compound VI, FIG. 1). Yellow solid; mp 50–54° C.; bp 109° C. 1H NMR δ (CDCl$_3$, 300MHz) 1.89(m,2H, CH$_2$CHCONH), 2.10–2.29 (m, 6H, CH$_2$CH$_2$CH$_2$), 3.04 (t, J=6.0 Hz, 2H, CONHCH$_2$CH$_2$S), 3.19 (t, J=7.4 Hz, 2H, SSCH$_2$CH$_2$NH$_2$), 3.25 (m, 10H, CH$_2$NH), 3.51 (t, J=6.5 Hz, 2H, SSCH$_2$CH$_2$NH$_2$), 3.78 (m, 2H, CONHCH$_2$CH$_2$S), 4.11 (t, J=6.7 Hz, 1H, CHCONH). M (for C$_{15}$H$_{41}$ON$_8$S$_2$)= 380.62; m/z (LSIMS)=381.24.

Synthesis of N-(2-Mercaptoethyl)spermine-5-Carboxamide [MESC]—DESC was dissolved in 50 mM sodium phosphate buffer, pH 8.0, containing 250 mM dithiothreitol (DTT), and incubated for 30 minutes at 37° C. in a water bath. The mixture was then loaded on a Dowex™ 50W-X4 cation exchange column equilibrated with H$_2$O, and after washing with 5 column volumes each of 1 N HCl and 2 N HCl, the free thiol was eluted with 10 volumes of 4 N HCl. Amine-containing fractions, as identified by mixing 5 μl aliquots with 200 μl of an o-phthaldialdehyde solution (3.7 mM o-phthaldialdehyde; 0.4 M boric acid, pH 10.4; 1% v/v MeOH; 0.45% v/v 2-mercaptoethanol; 0.03% w/v Brl] 35) and heating for 20 minutes at 37° C., were then pooled. The amount of N-(2-mercaptoethyl)-spermine-5-carboxamide [MESC] tetrahydrochloride (compound VII, FIG. 1) thus isolated was titrated for thiol equivalents with 5,5'-dithiobis-(2-nitrobenzoic acid) (Jocelyn, P. C. 1987. *Meth. Enzymol.* 143, 44–67) using either cysteamine or DTT as standard. The yield of MESC using this procedure was virtually 100%, based on the number of thiol equivalents determined with 5,5'-dithio-bis-(2-nitrobenzoic acid) and the expected number of thiol equivalents expected per mass of DESC. Finally, MESC purity was confirmed by ion-pair reversed-phase HPLC using post-column derivatization with o-phthaldialdehyde (Pegg, A. E., Wechter, R., Poulin, R., Woster, P. M. and Coward, J. K. 1989. *Biochemistry* 28: 8446–8453). $^1$NMR δ (CDCl$_3$, 300 MHz) 1.91 (m, 2H, CH$_2$CHCONH), 2.08–2.24 (m, 6H, CH$_2$CH$_2$CH$_2$), 2.82 (t, J=6.3, 2H, CONH CH$_2$CH$_2$SH), 3.22 (m, 10H, CH$_2$NH, 3.56 (m, 2H, CONHCH$_2$ CH$_2$ SH), 4.11 (t, J=6.6, 1H, CHCONH).

Synthesis of Thioether Adducts of MESC with iodoacetamides—To 1 ml of an extemporaneously prepared, DTT-free solution of MESC (20 mM in H$_2$O) were added 50 μl of 50 mM Tris-HCl (pH 7.0) and 105 μl of a 40 mM solution of either iodoacetamide, LY iodoacetamide or ASIB in a light-protected microcentrifuge tube, and the mixture was incubated for 2 hours at 37° C. The extent of thiol modification was assessed by measuring the amount of thiol remaining at the end of the incubation with 5,5'-dithio-bis- (2-nitrobenzoic acid) as described above, and was determined to be essentially complete. Excess iodoacetamide was then inactivated by adding DTT to a final concentration of 40 mM and incubating the solution for 2 hours at 37° C. The resulting solutions of MESC adduct was used without further purification for [$^3$H]spermidine uptake assays conducted as described below. The effect of the respective DTT-inactivated iodoacetamide on spermidine transport was determined in parallel by incubating cells with the same reaction mixture from which MESC was omitted.

Cell culture—Both ZR-75-1 human breast cancer cells and Chinese hamster ovary cells (CHO-K1) were obtained from the American Type Culture Collection (Rockville, Md.). ZR-75-1 cells were maintained in phenol red-free RPMI 1640 medium supplemented with 10% fetal bovine serum, 2 mM L-glutamine, 1 mM sodium pyruvate, 15 mM Hepes, 10 nM 17β-estradiol, and antibiotics [MEZR medium] (Huber, M. and Poulin, R. 1995. *Cancer Res.* 55, 934–943). CHO-K1 cells were routinely grown in α-Minimal Essential Medium supplemented with 10% Cosmic™ calf serum in a 5% $CO_2$ humid atmosphere at 37° C.

Effect of Inhibitors on Cell Proliferation—For growth studies, ZR-75-1 cells were cultured in MEZR medium or in phenol red-free RPMI 1640 supplemented with 2 mM L-glutamine, 1 mM sodium pyruvate, 15 mM Hepes, antibiotics, 1 nM 17β-estradiol, 0.5 μg of bovine insulin per ml and 5% (v/v) charcoal-treated fetal bovine serum (SD medium), as indicated in the text. When polyamines or polyamine analogs were added to serum-containing media, 1 mM aminoguanidine was added to inhibit bovine serum amine oxidase (BSAO) activity (Morgan, D. M. L. 1989. in *The Physiology of Polyamines* (Bachrach, U., and Helmer, Y. M. eds) Vol. I, pp. 203–229, CRC Press, Boca Raton). The effect of the transport inhibitors on cell growth was measured by incubating ZR-75-1 cells for 11 days in medium supplemental with antagonist, polyamines and/or 1 mM DFMO as indicated, followed by colorimetric determination of DNA content with 3,5-diaminobenzaic acid (Simard, J., Dauvois, S., Haagensen, D. E., Lévesque, C., Mérand, Y. and Labrie, F. 1990. *Endocrinology* 126: 3223–3231). Medium was changed every other day in these experiments because of the slow reaction of the compound with an unknown component present in the IMEM and RPMI 1640 medium formulation.

Polyamine Analysis—ZR-75-1 cells were plated in 100 mm culture dishes at 5×10$^5$ cells/dish in MEZR medium and grown for 5 days with medium changes every other day. Fresh MEZR medium containing the indicated concentration of transport antagonist was then added, plus or minus 200 μM cycloheximide (CHX), and cells were incubated for 1 or 6 hours. Medium was then removed, cell monolayers rinsed twice with 10 ml of ice-cold $Ca^{2+}/Mg^{2+}$-free phosphate buffered-saline (PBS) (2.7 mM KCl; 1.5 mM $KH_2PO_4$, 8.1 mM $Na_2HPO_4$; 137 mM NaCl), and harvested by centrifugation (2000×g×90 s at 4° C.) following a 5 to 7 minute-incubation with bovine trypsin/EDTA solution (0.05%/0.02%, w/v) in Hanks' Balanced Salt Solution (Huber, M. and Poulin, R. 1995. *Cancer Res.* 55: 934–943). Cell pellets were resuspended in 300 μl of 10% (v/v) trichloroacetic acid or Tris-DTT buffer (50 mM Tris/HCl, 0.1 mM EDTA, 5 mM DTT, pH 7.5) and stored at −20° C. until further analysis. For chromatographic analysis, samples were first quickly thawed and incubated for 15 minutes at 37° C. Trichloroacetic acid was then added to DTT-containing samples to a final concentration of 10% (wt/v). Samples were dispersed for 2 minutes in a sonicating water bath, and pelleted in a microcentrifuge for 5 minutes. The trichloroacetic acid-insoluble pellet was solubilized in 300–500 μl of 1 N NaOH and used to determine protein content using bovine serum albumin (fraction V) as standard. Polyamine contents were then analyzed by ion pair reverse-phase HPLC with fluorometric detection after post-column derivatization with o-phthalaldehyde as described (Pegg, A. E., Wechter, R., Poulin, R., Woster, P. M., and Coward, J. K. 1989. *Biochemistry* 28: 8446–8453; Huber, M., and Poulin, R. 1995. *Cancer Res.* 55: 934–943). In this system, putrescine, spermidine, spermine, DEASC and DESC were resolved with retention times of 18.5, 31.0, 35.0, 36.5, 37.5 and 44.0 minutes respectively.

DESC stability—DESC stability was tested by incubating the compound dissolved (at 50 μM) in PBS or in IMEM medium containing 10% (v/v) fetal bovine serum plus or minus 1 mM aminoguanidine in a humid 5% $CO_2$ atmosphere at 37° C. and in the absence of cells. At indicated times, trichloroacetic acid was added to aliquots of this solution to a final concentration 10% (w/v) and the samples directly analyzed by HPLC as above.

Determination of Polyamine Uptake Activity—The rate of putrescine and spermidine transport was determined in ZR-75-1 cells incubated in serum-free RPMI 1640 medium as described (Lessard, M., Zhao, C., Singh, S. M. and Poulin, R. 1995. *J. Biol. Chem.* 270: 1685–1694), using [$^3$H]putrescine (30 Ci/mol) and [$^3$H]spermidine (20 Ci/mol), respectively as substrates for a 20 minute-assay period. Spermine uptake was similarly determined, using 1 μM [$^{14}$C]spermine (32 Ci/mol) as substrate. Uptake activity was expressed per amount of DNA as flurometrically determined using 3,5-diaminobenzoic acid (Simard, J., Dauvois, S., Haagensen, D. E., Lévesque, C., Mérand, Y. and Labrie, F. 1990. *Endocrinology* 126: 3223–3231). For the determination of spermidine uptake activity in CHO-K1 cells, 80% confluent cell monolayers were rinsed twice with PBS and incubated for 20 minutes at 37° C. in 400 μl of buffer A (20 mM Tris-HCl, pH 7.4; 0.42 mM $CaCl_2$; 0.41 mM $MgSO_4$; 103 mM NaCl; 5.7 mM KCl; 1.1 mM D-glucose) containing 5 μM [$^3$H]spermidine (20 Ci/mol). Cell cultures were then washed twice with 1 ml PBS containing 5.7 mM sym-norspermidine. Cells were then lysed with 200-μl aliquot of 1 N NaOH and incubated for 30 minutes at 60° C. After neutralization with 200 μl of 1 N HCl, radioactivity was determined from a 250-μl of the cell lysate by scintillation counting. Uptake activity was expressed per amount of total cellular protein as determined by the method of Bradford (Bradford, M. M. 1976. *Anal. Biochem.* 72: 248–254). Non-specific binding of radioactive substrate was similarly determined in parallel for both cell lines after a 15 second-incubation with 400 μl of ice-cold uptake solution.

Kinetic analyses—Kinetic analysis of polyamine transport was performed be determining uptake activity in the presence of 3 μM [$^3$H]putrescine or 1 μM [$^3$H]spermidine plus increasing concentrations of nonradioactive substrate. $K_m$, $K_i$ and $V_{max}$ values were then estimated by Line-weaver-Burke analysis. For competitive inhibitors, $K_i$ values were also estimated by measuring uptake activity in the presence of logarithmically increasing concentrations of antagonist, and using the Cheng-Prusoff equation (Cheng. Y. -C. and Prusoff, W. H. 1973. *Biochem. Pharmacol.* 22: 3099–3108) by iterative curve fitting for a sigmoidal curve. For mixed competitive/noncompetitive inhibition, two methods were used to calculate kinetic constants. First, the equation $$v = \frac{V_{max}}{\frac{K_m}{s}\left(1+\frac{i}{K_i}\right)+\left(1+\frac{i}{K_i'}\right)}$$

where v, s, and i are the transport velocity, substrate concentration and inhibitor concentration respectively, was used to calculate the inhibition constants for inhibitor/carrier complex formation ($K_i$) and carrier/inhibitor substrate complex formation ($K_i'$) (Dixon, M. and Webb, E. C. 1976. *Enzymes*, 3rd Ed., Academic Press, San Diego, Calif.). Alternatively, the value of $K_i$ for a mixed competitor/non-competitor was estimated from the intersect of equations of $v^{-1}$ vs i at two different substrate concentrations (Dixon, M. and Webb, E. C. 1976. *Enzymes*, 3rd Ed., Academic Press, San Diego, Calif.).

Intracellular Accumulation

The time course of intracellular accumulation of spermidine in the presence of transport antagonists was determined by incubating ZR-75-1 cells in 24-well plates with DESC (50 or 200 μM) or MESC (200 μM) in dissolved in MEZR medium containing 5 μM [$^3$H]spermidine in the presence or absence of cycloheximide (CHX, 200 μM), and harvesting at the indicated times for the determination of intracellular radioactive contents, as described above for polyamine uptake assays.

Statistical Analysis

Statistical significance of differences between means was assessed by unpaired Student's t-tests. Unless otherwise indicated, results are expressed as means±SD of determinations from triplicate cell cultures.

Design and Synthesis of DESC, DEASC, and MESC

The original rationale for synthesizing MESC (Compound VII of FIG. 1) was to generate an affinity reagent with a thiol side chain that could be derivatized with fluorescent or radioactive sulfhydryl reagents to label the polyamine transporter. The precursor chosen for the synthesis, namely 5-carboxyspermine, has been previously used to prepare lipopolyamines for efficient DNA transfection (Behr, J. P. 1989. *J. Chem. Soc., Chem. Commun.* 101–103; Behr, J. P., Demeneix, B., Loeffler, J. -P. and Perez-Mutul, J. 1989. *Proc. Natl. Acad. Sci. USA* 86:6982–6986), and more recently, as a photoaffinity reagent to label the polyamine-binding site of casein kinase 2 (Leroy, D., Schmid, M., Behr, J. -P., Filhol, O., Pares, S., Garin, J., Bourgarit, J. -J., Chambaz, E. M. and Cochet, C. 1995. *J. Biol. Chem.* 270:17400–17406). The scheme used to prepare MESC involved the coupling of a cystamine bridge through amide bonds with two Boc-protected 5-carboxyspermine molecules to form DESC after removal of the Boc groups (Compound V of FIG. 1), followed by reduction of the DESC disulfide bridge. A small amount (10–15%) of the mixed MESC-cysteamine disulfide (DEASC, Compound VI; FIG. 1) was also generated in the coupling process. Complete separation of DEASC from DESC on a preparative basis proved to be difficult even using ion exchange chromatography (data not shown). Consequently, most DESC preparations contained a small amount (1–2%) of DESC after reversed-phase liquid chromatography on $C_{18}$ silica gel. DESC and DEASC were stable for months in aqueous solutions buffered at pH=7.0, whereas MESC solutions were supplemented with DTT to prevent oxidation.

Figure 2:
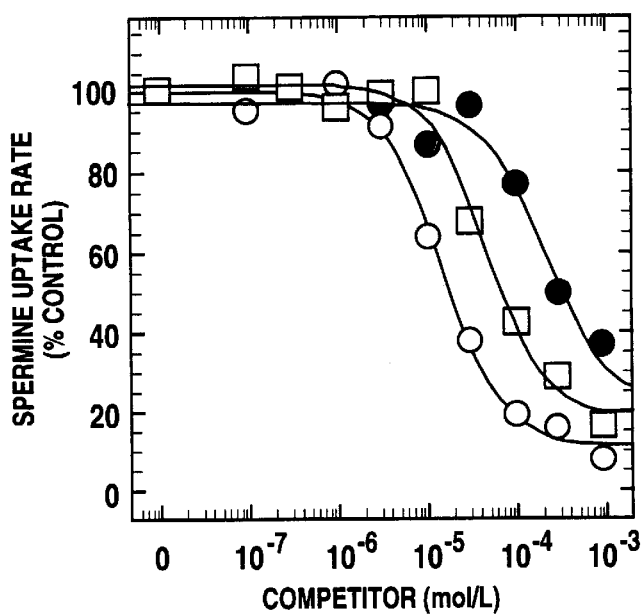
FIG. 2 graphically illustrates the inhibition of [$^{14}$C] spermine transport by MESC, DESC and DEASC in human ZR-75-1 breast cancer cells. The rate of spermine uptake was measured in ZR-75-1 cells grown as monolayers in 24-well culture plates in the presence of the indicated concentrations of DESC (○), MESC (●), and DEASC (□), using 1 μM [$^{14}$C]spermine as substrate. Data are the mean±SD of triplicate determinations.
Figure 3A:
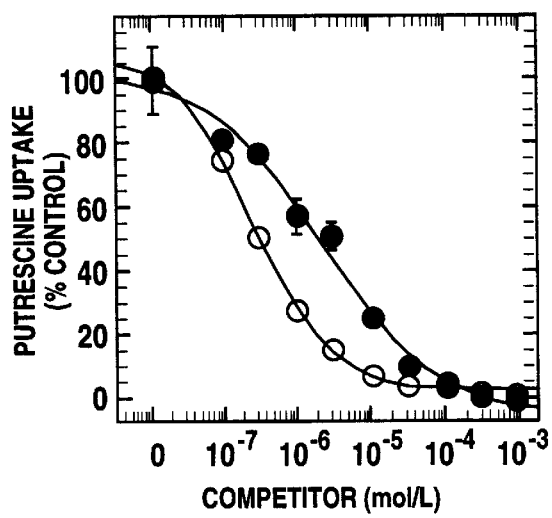
FIG. 3 graphically illustrates the inhibition of [$^3$H] spermidine uptake by spermine and DESC in ZR-75-1 cells. The rate of spermidine uptake was measured in ZR-75-1 cells grown as monolayers in 24-well culture plates in the presence of the indicated concentrations of spermine (○) and DESC (●) using 3 μM [$^3$H]putrescine (A) or 1 μM [$^3$H]spermidine (B) as substrate. Data are the mean±SD of triplicate determinations from a representative experiment.
Figure 3B:
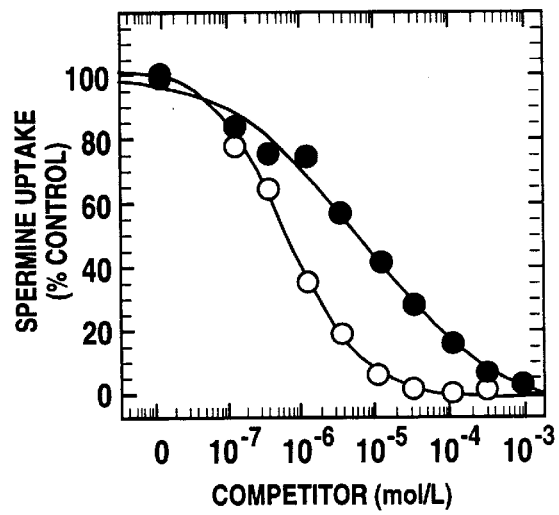
Figure 4A:
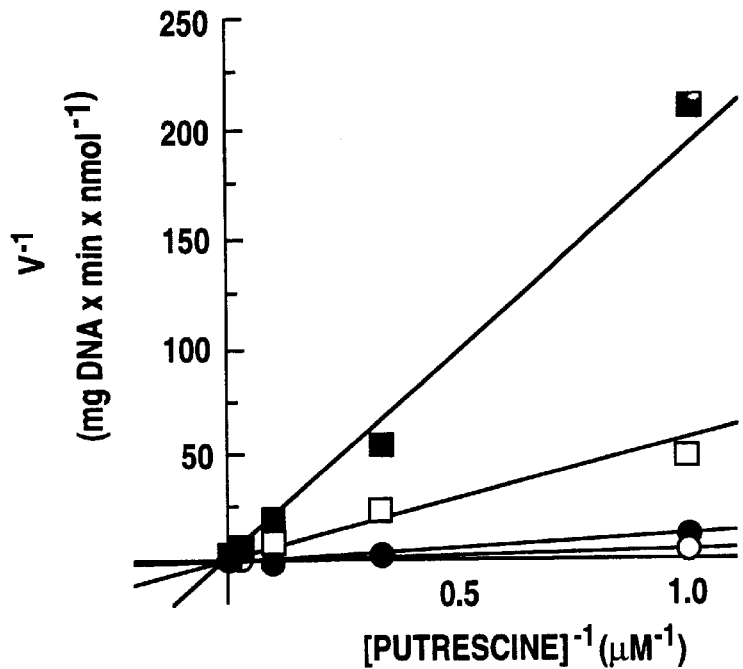
FIG. 4 illustrates graphically the Lineweaver-Burke analysis of putrescine transport inhibition by DESC and DEASC in ZR-75-1 cells. the rate of [$^3$H]putrescine uptake was determined in ZR-75-1 cell cultures with increasing concentrations of substrate (A) in the presence of 0 μM DESC (○), 3 μM DESC (●), 30 μM DESC (□) or 100 μM DESC (■) or (B) in the presence of 0 μM DEASC (○), 20 μM DEASC (●), 50 μM DEASC (□) or 200 μM DEASC (■)
Figure 4B:
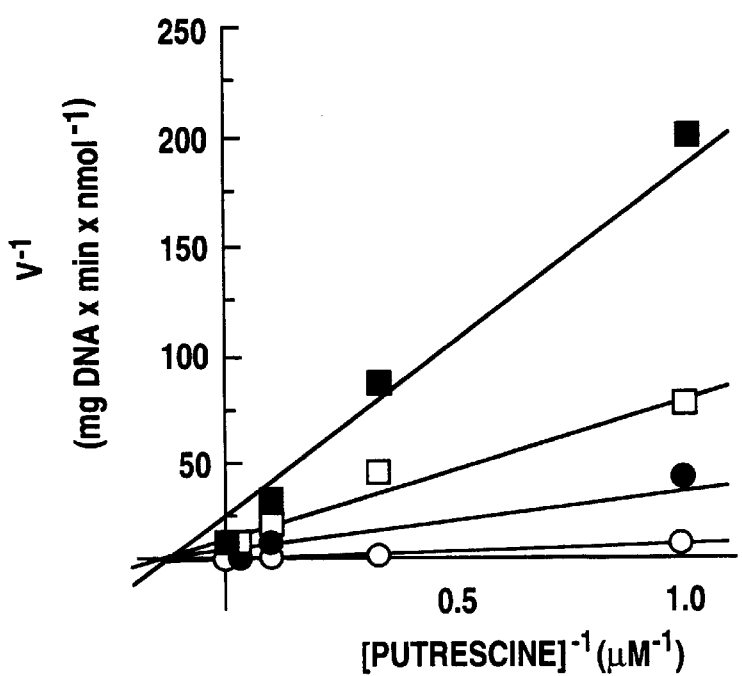

Affinity of DESC, DEASC and MESC for the Mammalian Diamine and Polyamine Transport In order to evaluate the suitability of the spermine conjugates as prospective affinity ligands, their relative ability to inhibit putrescine and polyamine uptake was evaluated. As shown in FIG. 2, DESC was the most potent antagonist of [$^{14}$C]spermine transport in ZR-75-1 cells, with a $K_i$ value about 5-fold and 16-fold lower than that of DEASC and MESC, respectively. The ability of spermine to compete against [$^3$H]putrescine and [$^3$H]spermidine uptake was in fact only about 7-fold higher than that of DESC (FIG. 3). DESC (FIG. 4A) and MESC (data not shown) were pure competitive inhibitors of [$^3$H]putrescine uptake at concentrations up to 100 and 200 μM, respectively. On the other hand, inhibition of putrescine transport by DEASC belonged to a mixed competitive/non-competitive type (FIG. 4B). Table I summarizes the $K_i$ values determined for DESC, MESC and DEASC toward putrescine, spermidine and/or spermine uptake, in relation with the mutual transport interactions between the latter substrates. Notably, $K_i$ values of the three spermine conjugates with respect to putrescine uptake were 3-fold to 5-fold higher than for spermine uptake, unlike spermidine and spermine which both inhibited the uptake of either substrate with similar potency, and with a $K_i$ roughly equal to their $K_m$ as substrate.

TABLE I $K_i$ Values of inhibition of Diamine and Polyamine Transport by MESC, DESC and DEASC in ZR-75-1 Cells

| Compound | $K_m$ or $K_i$ (μM) | | |
| --- | --- | --- | --- |
| | Putrescine | Spermidine | Spermine |
| Putrescine | 3.7 ± 0.4[a] | 125 ± 29[a] | 0.23 ± 0.13[a,b] |
| Spermidine | 0.23 ± 0.05[a] | 0.49 ± 0.15[a] | 0.37 ± 0.09[a] |
| Spermine | 0.33 ± 0.02[a] | ND | 0.20 ± 0.06[a] |
| DESC | 1.6 ± 0.5[b] | 2.7 ± 1.1[b] | 5.0 ± 0.7[b] |
| MESC | 22 ± 3[b] | ND | 80 ± 31[b] |
| DEASC | 5.3 ± 0.6 ($K_i$)[c] 4.1 ± 0.5 ($K_i'$) | ND | 16 ± 3[d] |

Data annoted with a are from Lessard, M., Zhao, C., Singh, S. M., and Poulin, R. 1985. *J. Biol.* 270:1685–1694, b indicates data obtained with this work; mean±SD of triplicate determinations from 2 to 4 different experiments; c corresponds to values of inhibition constants for carrier/inhibitor complex formation ($K_i$) and for carrier/inhibitor/putrescine complex formation ($K_i'$) assuming a mixed competitive/non-competitive model; mean±SD of triplicate determinations ad 3 three inhibitor concentrations; data annoted with d correspond to value of $K_i$ determined at two different substrate concentrations for a series of increasing inhibitor concentrations (Dixon, M., and Webb, E. C. 1976. *Enzymes*, 3rd Ed., Academic Press, San Diego, Calif.).

The relative potency of DESC and MESC as competitive inhibitors of polyamine uptake was also evaluated in CHO-K1 cells, in which they respectively exhibited $K_i$ values of 0.92±0.15 and 33.6±7.2 μM (FIG. 5).

Effect of Side Chain Length and Substituents on Spermidine Transport Inhibition by MESC Derivatives The observation that MESC was a less potent inhibitor of diamine and polyamine transport than DESC or DEASC suggested that the nature of the side chain strongly influences the interaction of these compounds with the carrier. The thiol side chain of MESC was thus derivatized with substituting groups of different sizes and charges through thioether linkage with three different iodoacetamides, namely LY iodoacetamide, ASIB and iodoacetamide itself, and the ability of the resulting complexes (MESC-LY, MESC-ASIB and MESC-acetamide, respectively) to inhibit spermidine uptake was then evaluated. These studies were conducted using CHO-K1 cells. As shown in FIG. 5, derivatization of the thiol group of MESC did not signicantly (P>0.10) increase the $K_i$ toward spermidine uptake for the three conjugates studied. In the case of MESC-ASIB, $K_i$ values might have been underestimated by partial inactivation of the polyamine carrier at the assay temperature, although the uptake reaction was conducted under subdued lighting. Thus, the results show that specific recognition of the spermine head of MESC can accomodate considerable variation in length, size, polarity or charge for the side chain without detrimental effect on its affinity for the polyamine carrier. Consequently, inhibitors having different side chains, while maintaining their inhibitory activity on polyamine transport are also encompassed by the present invention.

Lack of Permeation of DESC and MESC through the Polyamine Transport System

The ability of ZR-75-1 cells to accumulate DESC and MESC was determined. Since DESC was eluted as a late, broad peak in the HPLC system used, DTT was added to cell extracts to reduce DESC to MESC and decrease the detection threshold. Results are shown in Table II. ZR-75-1 cells were incubated for 1 or 6 hours in MEZR medium in the presence of 50 or 200 $\mu$M DESC or MESC prior to determination of polyamine contents. CHX was added at 200 $\mu$M where indicated. Other details are provided under "Materials and Methods". Values are the mean±SD of triplicate determinations from 2 independent experiments.

TABLE II

Intracellular Accumulation of DESC and MESC in ZR-75-1 Cells

| Addition | Time (h) | Polyamine intracellular contents (nmol/mg protein) | | | |
|---|---|---|---|---|---|
| | | Spermidine | Spermine | DESC | MESC |
| Control | 1 | 0.69 ± 0.08 | 8.22 ± 0.48 | — | — |
| | 6 | 0.91 ± 0.07[a] | 9.16 ± 0.13 | — | — |
| +50 $\mu$M DESC | 1 | 0.81 ± 0.14 | 8.27 ± 0.81 | <0.01 | <0.01 |
| | 6 | 0.73 ± 0.11 | 8.60 ± 0.29 | <0.01 | <0.01 |
| +200 $\mu$M DESC | 1 | 0.79 ± 0.11 | 8.77 ± 0.79 | <0.01 | <0.01 |
| | 6 | 0.76 ± 0.11 | 8.66 ± 0.26 | 0.12 ± 0.01 | <0.01 |
| +200 $\mu$M DESC ++CHX | 1 | 0.76 ± 0.04 | 9.57 ± 0.31 | <0.01 | <0.01 |
| | 6 | 0.70 ± 0.03 | 9.55 ± 0.13 | 0.10 ± 0.01 | <0.01 |
| +50 $\mu$M MESC | 1 | 0.95 ± 0.11 | 7.77 ± 0.06 | <0.01 | <0.01 |
| | 6 | 0.75 ± 0.11 | 8.13 ± 0.17 | <0.01 | <0.01 |
| +200 $\mu$M MESC | 1 | 1.15 ± 0.07[a] | 8.93 ± 0.53 | <0.01 | 0.020 ± 0.005 |
| | 6 | 0.81 ± 0.15 | 8.32 ± 0.43 | <0.01 | 0.13 ± 0.06 |

[a]Significantly different (P < 0.5) from control value at time = 1h. (?)

As shown in Table II, only trace amounts of DESC could be recovered in ZR-75-1 cells after a 6-hour incubation with 200 $\mu$M, but not with 50 $\mu$M; DESC could be detected only after reduction with DTT. These levels represent only about 1.5% of the accumulation measured in ZR-75-1 cells under identical conditions for various substrates, including spermidine, sym-norspermidine and spermine (Lessard, M., Zhao, C., Singh, S. M. and Poulin, R. 1995. *J. Biol. Chem.* 270:1685–1694). Moreover, inhibition of protein synthesis by cyclohexamide (CHX), which is known to upregulate polyamine uptake by preventing the synthesis of a polyamine-induced feedback repressor of transport (Lessard, M., Zhao, C., Singh, S. M. and Poulin, R. 1995. *J. Biol. Chem.* 270:1685–1694; Mitchell, J. L. A., Diveley, R. R., Jr. and Bareyal-Leyser, A. 1992. *Biochem. Biophys. Res. Commun.* 186:81–88), did not enhance DESC internalization, in marked contrast with its effect on spermidine accumulation under similar conditions (FIG. 6B) (Lessard, M., Zhao, C., Singh, S. M. and Poulin, R. 1995. *J. Biol. Chem.* 270:1685–1694). Likewise, MESC was accumulated to measurable levels by ZR-75-1 cells only when present at 200 $\mu$M (cf. Table II). Thus, neither DESC or MESC appear to be used as substrates for the polyamine transport system despite the high affinity of the former compound as an antagonist of diamine and polyamine uptake.

Effect of DESC and MESC on Intracellular Polyamine Accumulation

Figure 6A:
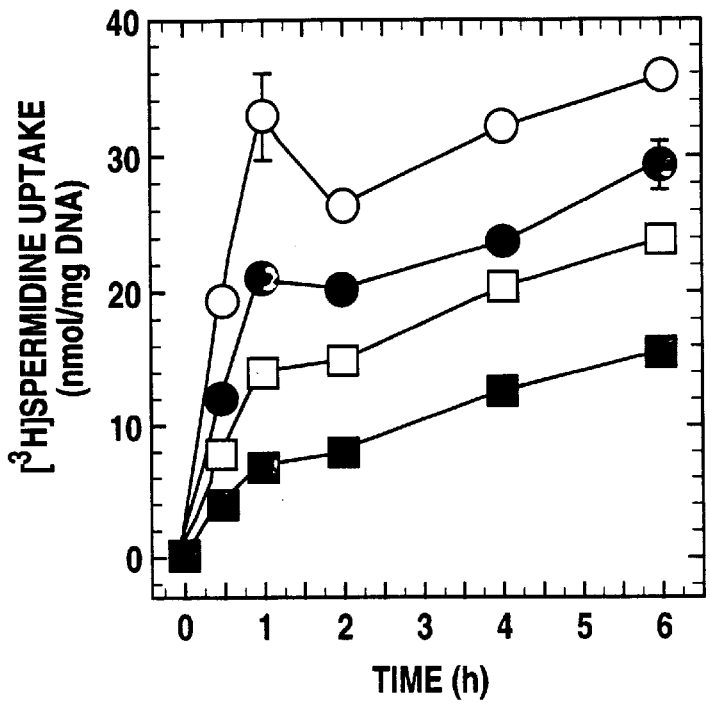
FIG. 6 graphically represents the effect of DESC and MESC on the intracellular accumulation of [$^3$H]spermidine in ZR-75-1 cells, wherein at time 0 (A), 5 μM [$^3$H] spermidine was added to ZR-75-1 cell cultures grown in 24-well plates (1 ml/well) in the presence of 200 μM MESC (574 ), 50 μM DESC (□) or 200 μM DESC (■), and accumulation of radiolabeled spermidine determined after the indicated interval. Control cells (○) received vehicle only. B, same as in A, except that 200 μM CHX was added at time 0 in the presence of 0 (●), 50 (□) or 200 μM DESC (■). Data are the mean±SD of triplicate determinations.
Figure 6B:
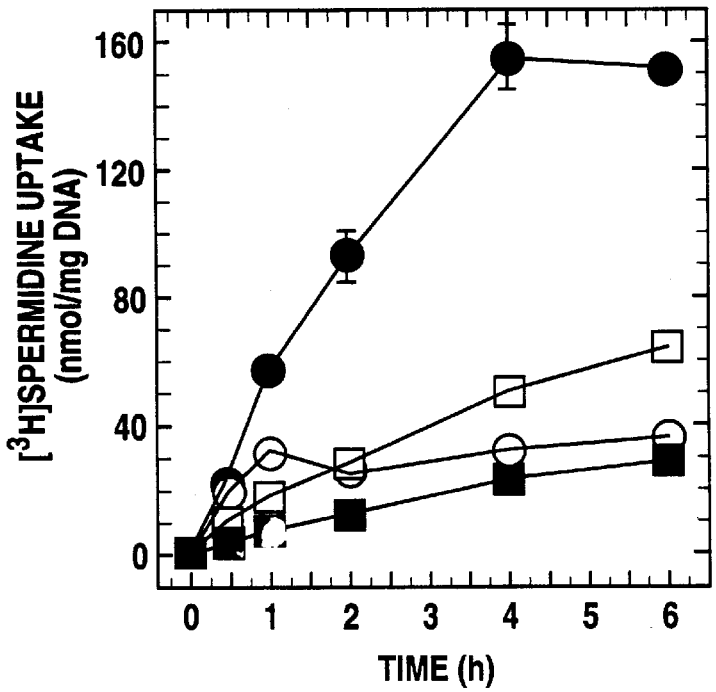

To further evaluate the capacity of DESC and MESC to block polyamine uptake, the time course of internalization of radiolabeled spermidine was determined in ZR-75-1 cells incubated for up to 6 hours in the presence of the impermeant agonists. As illustrated in FIG. 6A, steady-state [$^3$H]spermidine accumulation in the absence of competitor abruptly reached a near plateau after about 1 hour, which results from the induction of feedback inhibition of polyamine transport (Lessard, M., Zhao, C., Singh, S. M. and Poulin, R. 1985. *J. Biol. Chem.* 270:1685–1694). MESC and DESC decreased the initial rate of spermidine uptake according to their respective potency as competitive antagonists. Interestingly, spermidine accumulation in the presence of either inhibitor followed a pattern similar to that of control cells, i.e. a rapid phase during the first 60 minutes, followed by a much slower rate of accumulation thereafter, which was nearly independent of antagonist concentration. This pattern suggests that even cellular levels of newly internalized spermidine as low as 20% of those found under control conditions, e.g. in cells treated with 200 $\mu$M DESC, may induce a near maximal degree of feedback repression of polyamine transport. Nevertheless, even a 40-fold excess of the most potent antagonist (i.e. 200 $\mu$M DESC) only decreased net spermidine accumulation by only 50% after 6 hours. As previously observed (Lessard, M., Zhao, C., Singh, S. M. and Poulin, R. 1995. *J. Biol. Chem.* 270:1685–1694), CHX abolished the induction of feedback transport inhibition, resulting in a 4-fold increase in spermidine accumulation after 4 hours (FIG. 6B). Protein synthesis inhibition also enhanced spermidine accumulation in DESC-treated cells, a finding consistent with the onset of substantial feedback transport repression by subthreshold levels of internalized substrate. Thus, in the absence of the feedback mechanism, the highest concentration of DESC tested (200 $\mu$M) decreased net [$^3$H]spermidine accumulation by 80 to 85% after 6 hours and to a level lower than that found in control cells with a fully repressed uptake activity.

Effect of DESC, DEASC and MESC on Cell Proliferation

Figure 7:
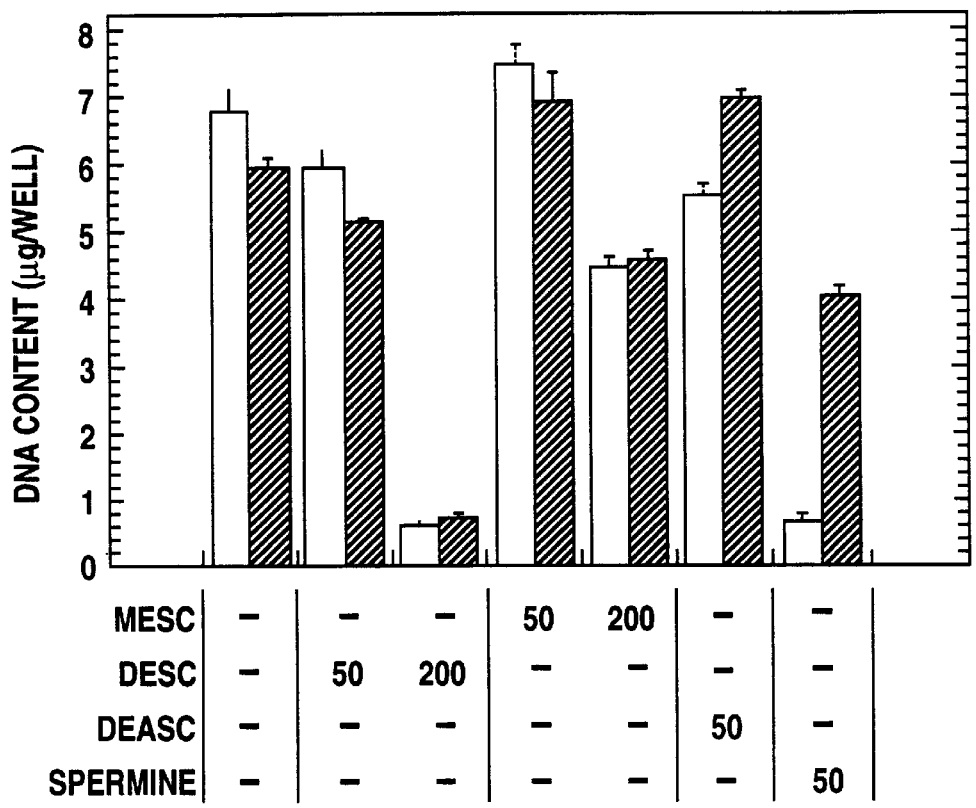
FIG. 7 illustrates the effect of spermine, MESC, DESC and DEASC on ZR-75-1 cell proliferations. Cells were incubated for 11 days in MEZR medium with the indicated concentration of spermine, DESC, MESC, or DEASC in the presence (shaded bars) or absence (plain bars) of 1 mM of aminoguanidine, and DNA content per culture was then determined. Data represent the mean±SD of triplicate determinations.

Due to the analogy of the novel transport antagonists with spermine, it might be surmised that they would exhibit significant cytotoxicity like the parent molecule. The marked toxicity of low (<10$^{-3}$M) spermine concentrations in biological media mostly results from catabolism by copper amine oxidases, which generates a dialdehyde, acrolein and $H_2O_2$ has deleterious products and can be irreversibly inhibited by carbonyl reagents such as aminoguanidine (Morgan, D. M. L. 1989. in *The Physiology of Polyamines* (Bachrach, U., and Heimer, Y. M. eds) Vol. I, pp. 203–229, CRC Press, Boca Raton). The biocompatibility of DESC, MESC and DEASC was thus evaluated during a long-term (11-day) incubation with ZR-75-1 cells grown in RPMI 1640 containing 10% (v/v) FBS in the absence and presence of 1 mM aminoguanidine. As shown in FIG. 7, aminoguanidine alone had a slight inhibitory effect on ZR-75-1 cell growth as previously observed (Huber, M. and Poulin, R. 1985. *Cancer Res.* 55:934–943). Although DESC was only mildly growth inhibitory at 50 $\mu$M, there was an abrupt, aminoguanidine-resistant increase in toxicity at 200 $\mu$M. In contrast, spermine was acutely cytotoxic at 50 μM, an effect that was only partly prevented by aminoguanidine. MESC was considerably less toxic than its dimer, with a 35% decrease in cell growth at 200 μM which was not blocked by aminoguanidine. On the other hand, 50 μM DEASC caused a 20% inhibition of cell proliferation which could be completely prevented by the amine oxidase inhibitor. Thus, DESC, and to a much lesser degree, its thiol monomer MESC, are cytotoxic toward breast cancer cells at high concentrations through a mechanism that does not involve BSAO. Weak growth inhibition caused by the mixed MESC-cysteamine disulfide, however, apparently involved degradation by a copper amine oxidase.

Figure 8:
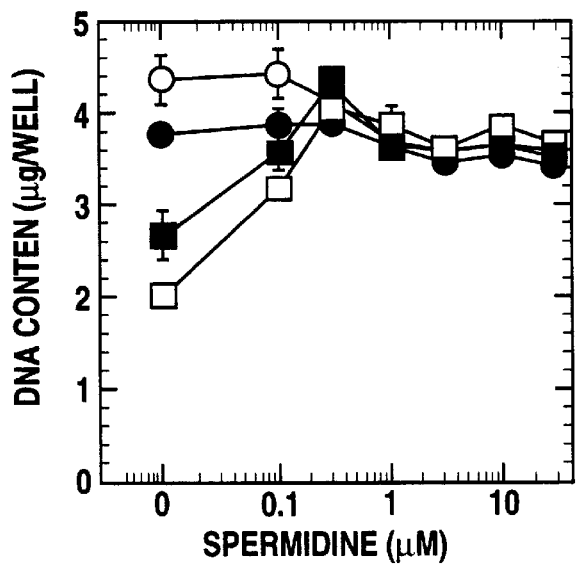
FIG. 8 represents the effect of DESC on the reversal of DFMO-induced growth inhibition by exogenous spermidine in ZR-75-1 cells. Cells were incubated for 11 days in SD medium with the indicated concentrations fo spermidine in the presence of 50 μM DESC (●), 1 mM DFMO (□), or the combination thereof (■), or in the absence of drugs (○). Data are the mean±SD of triplicate cultures.

Effect of DESC on Rescue of DFMO-Induced Growth Inhibition by Exogenous Spermidine Although DESC is indeed a potent antagonist of polyamine accumulation, the slow residual uptake that occured even at a 40-fold molar excess of inhibitor might be sufficient to counteract polyamine depletion by inhibitors of polyamine biosynthesis. This possibility was assessed by comparing the ability of DESC to prevent the reversal of DFMO-induced growth inhibition by increasing concentrations of exogenous spermidine. At concentrations superior to 0.3 μM, spermidine inhibited ZR-75-1 cell proliferation by up to 20% (FIG. 8). This effect could be due to an incomplete inhibition of BSAO by aminoguanidine (Seiler, N. 1987. in *Inhibition of Polyamine Metabolism. Biological Significance and Basis for New Therapies* (McCann, P. P., Pegg, A. E. and Sjoerdsma, A., eds.), pp 49–77, Academic Press, Orlando), since it was not observed in media supplemented with equine serum, which does not contain amine oxidase activity (Blaschko, H. and Hawes, R. 1959. *J. Physiol.* 145:124–131), instead of FBS (data not shown). The approximately 50% growth inhibition induced by 1 mM DFMO after an 11-day incubation was completely reversed by as little as 0.3 μM spermidine, whereas 0.1 μM spermidine already restored growth of DFMO-treated cells to 78% of control value. However, addition of 50 μM DESC was unable to prevent the reversal of DFMO-induced growth inhibition by spermidine, even at a DESC:spermidine ratio of 500. Essentially similar results were obtained using horse serum instead of FBS, or replacing RPMI 1640 medium, which contains 3.2 μM reduced glutathione that might undergo thiol/disulfide exchange with DESC, with thiol-free IMEM (data not shown).

Stability of DESC in Biological Media

Figure 9A:
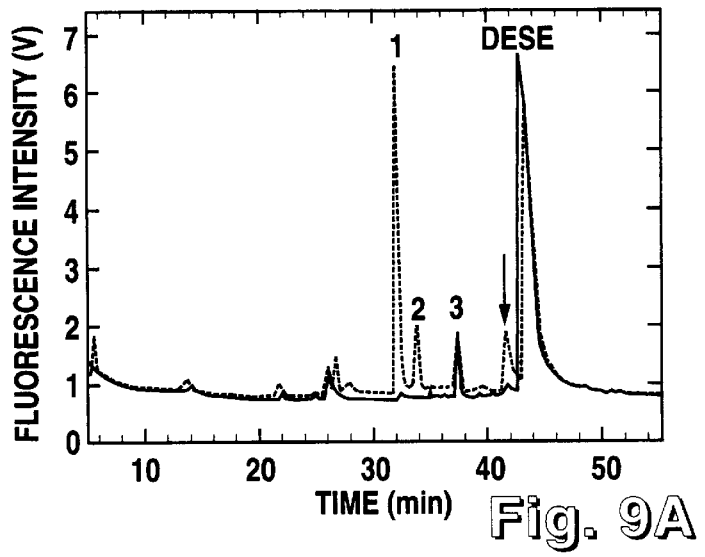
FIG. 9 represents the chromatographic profile of DESC and it degradation products in IMEM or PBS. DESC (50 μM) was added to 1 ml of IMEM containing 10% fetal bovine serum in the absence (A) or presence (B) of 1 mM aminoguanidine, or to 1 ml PBS (C) in 24-well culture plates in the absence of cells. Media were analyzed after 20 minutes (solid lines) or 48 hours (dotted lines) of incubation at 37° C. in a 95% air; 5% $CO_2$, water-saturated atmosphere for amine composition by ion-pair reversed-phase HPLC as described supra. Peaks 1 and 2 are degradation products of DESC, whereas peak 3 is a minor amount of DEASC initially present in the DESC preparation. Note the disappearance of peak 3 (DEASC) and the appearance of a shoulder (indicated by the arrow) at 42 minutes on the 48-hour profile in panel A.
Figure 9B:
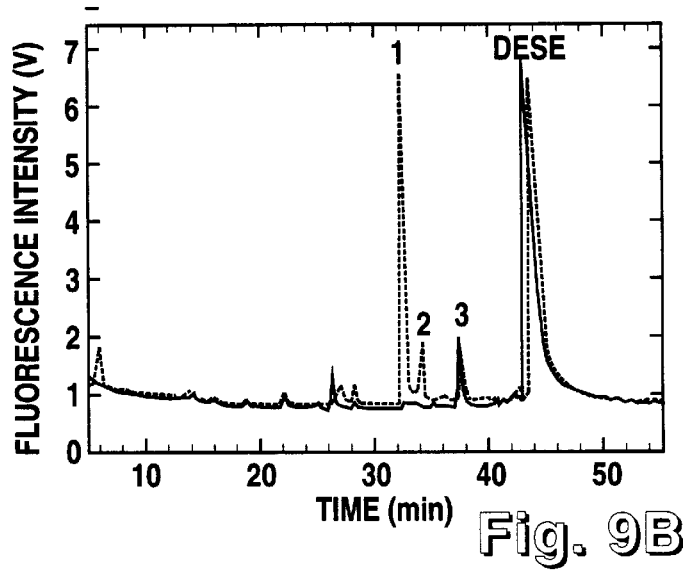
Figure 9C:
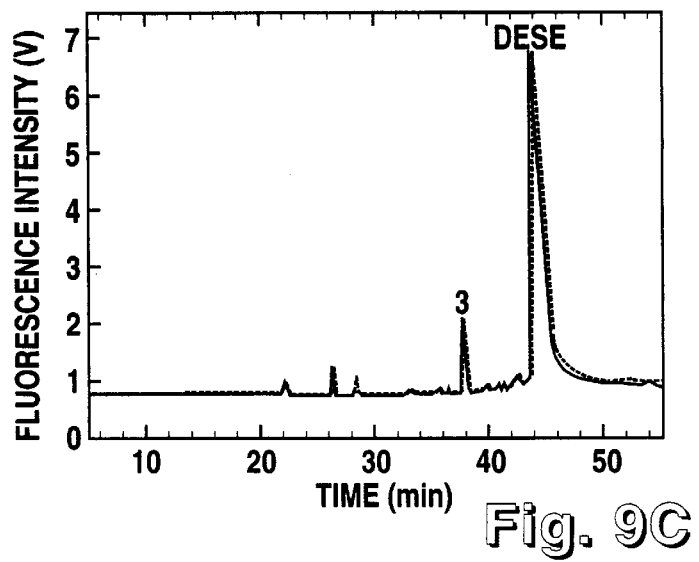
Figure 10:
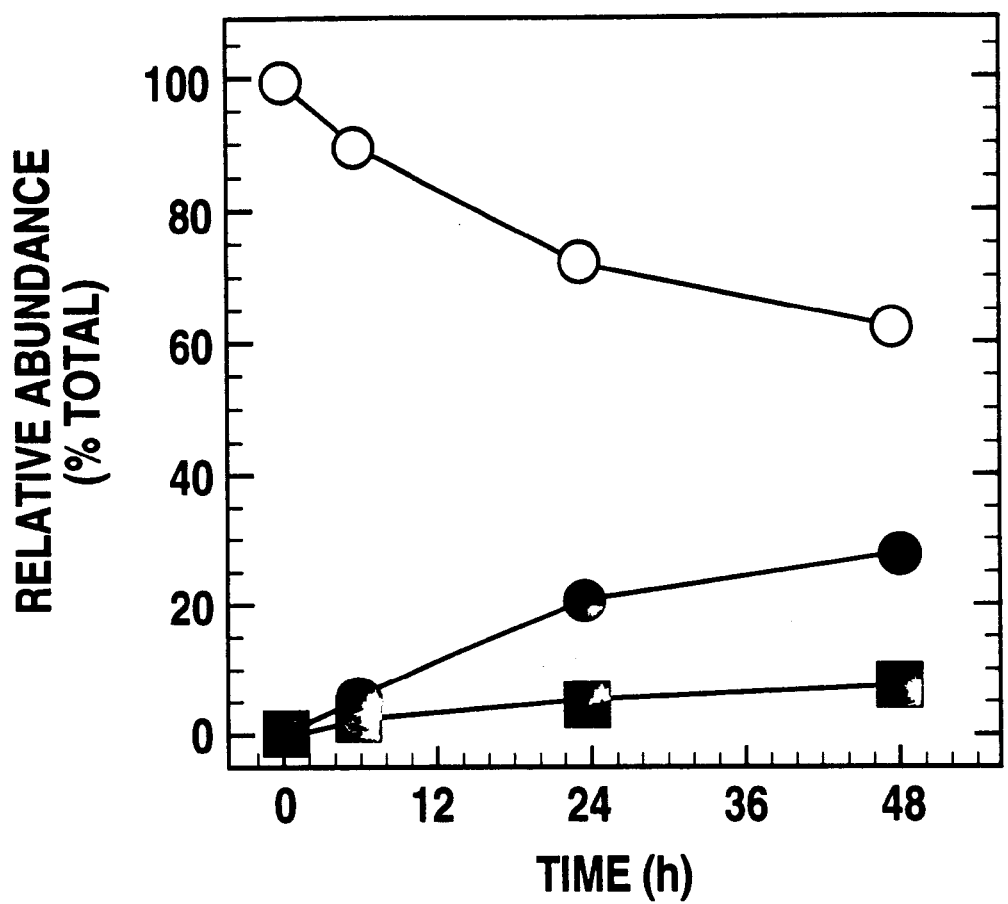
FIG. 10 represents the time course of degradation of DESC in growth medium. At time 0, 50 μM DESC was added to 1 ml of IMEM in 24-well culture plates and the content in DESC (○), compound 1 (Comp 1, ●) and compound 2 (Comp 2, □) determined by HPLC after the indicated incubation period at 37° C. in a 5% $CO_2$ atmosphere. Data represent the mean of triplicate determinations from a representative experiment.

The inability of DESC to block the biological effect of exogenous spermidine, even when present at large molar excesses, might have been caused by its degradation in growth media. To assess this hypothesis, DESC solutions (20 μM) made in PBS or in sterile IMEM medium enriched with 10% (v/v) FBS were incubated for 20 minutes or 48 hours under cell-free conditions at 37° C. in a humid 5% $CO_2$ atmosphere, and the polyamine analog was then analyzed by ion-pair reversed-phase HPLC. Indeed, after 48 hours, degradation of DESC to two new amine-containing derivatives occurred in IMEM (FIG. 9A, B) but not in PBS (FIG. 9C), as evidenced by the appearance of a major (compound 1) and minor (compound 2) peaks of o-phtaldialdehyde-reactive material eluting earlier than DESC. Although aminoguanidine did not prevent DESC degradation to the two unknown products, it did prevent the degradation of a trace amount of DEASC (indicated as compound 3) initially present in the DESC preparations, thus confirming that DEASC can indeed be a substrate of serum copper amine oxidase (FIG. 7). MESC could not be detected in these experiments, indicating that DESC does not undergo reduction to MESC under conditions used for cell culture. Furthermore, the decomposition of DESC in IMEM showed an identical pattern in the presence or absence of FBS (data not shown), which thus ruled out a serum component as being responsible for the degradation. FIG. 10 shows that DESC was slowly degraded to compounds 1 and 2. After 48 hours, i.e. the interval at which freshly made DESC-containing media were added to cell cultures in growth experiments, 40% of the DESC originally present had been decomposed by IMEM. Identical results were obtained using RPMI 1640 medium instead of IMEM (data not shown). Thus, an as yet unidentified component present in IMEM and RPMI 1640 medium, but not in PBS, must be responsible for the degradation of DESC.

DISCUSSION

We have shown that DESC, a novel type of spermine derivative, is endowed with high affinity for the polyamine transport system while being highly resistant to cellular uptake. The combination of these two attributes confers unique characteristics to DESC as a pure competitive antagonist of polyamine uptake.

As compared with spermine, the higher $K_i$ of MESC against putrescine, spermidine and spermine uptake could owe to the presence of an amide linkage, which decreases the basicity of the neighboring secondary amino group of the spermine head ($pK_a \approx 5.5$ in comparison with 8.9–9.8 for spermine) (Tabor, C. W. and Tabor, H. 1984. *Ann. Rev. Biochem.* 53:749–790; Remy, J. -S., Kichler, A., Mordvinov, V., Schuber, F. and Behr, J. -P. 1985. *Proc. Natl. Acad. Sci. USA* 92:1744–1748), and/or may cause steric hindrance for its interaction with the polyamine binding site (Bergeron, R. J. and Sellgsohn, H. W. 1986. *Bioinorg. Chem.* 14:345–355; Porter, C. W., Cavanaugh, P. F., Jr., Stolowich, N., Ganis, B., Kelly, E., and Bergeron, R. J. 1985. *Cancer Res.* 45:2050–2057). Nevertheless, despite the unfavorable structural features of MESC as a ligand, its dimerization into DESC increased by up to 20-fold the affinity of the resulting structure for the polyamine transporter. Although there is no precedent for dimeric polyamine structures like DESC, its overall design is reminiscent of that of 2-N-4-(1-azi-2,2,2-tri-flouroethyl)benzoyl-1,3-bis(D-mannos-4-yloxy)-2-propylamine, an impermeant ligand which binds to the exofacial domain of facilitative glucose transporters and bears two symmetrical sugar moieties linked tail to tail (Clark, A. E. and Holman, G. D. 1990. *Biochem. J.* 269:615–622). It is noteworthy that at least one mammalian glucose transporter, namely GLUT-1, exists as a tetrameric complex in its native form (Hebert, D. N. and Carruthers, A. 1992. *J. Biol. Chem.* 267:23829–23838; Gould, G. W., and Holman, G. D. 1993, *Biochem. J.* 295:329–341). It is therefore conceivable that the stronger affinity of DESC relative to MESC could reflect a dyad symmetry in the organization of the transporter complex. Alternatively, dimerization of MESC into DESC could impose conformational constraints (e.g. due to electrostatic repulsion) that would favor recognition of the polyamine binding site of the carrier by each of the symmetrical spermine moieties.

Interestingly, MESC thioethers as diverse in size as MESC-LY, MESC-ASIB or MESC-acetamide had $K_i$ values virtually identical to that of MESC, indicating that the thiol group of MESC does not specifically determine its lower affinity as a polyamine transport inhibitor as compared with DESC. Moreover, these data suggest that additional bulk on the side chain has little influence on the interaction of MESC with the polyamine transporter, in agreement with the observation that large substituents attached to the distal end of a spacer of sufficient length do not notably decrease the affinity of spermidine as a substrate for uptake (Holley, J. L., Mather, A., Wheelhouse, R. T., Cullis, P. M., Hartley, J. A., Bingham, J. P., and Cohen, G. M. 1982. *Cancer Res.* 52:4190–4195). Unexpectedly, the MESC-cysteamine mixed disulfide (DEASC) was found to block putrescine uptake as a mixed competitor/non-competitor, whereas MESC and DESC behaved like pure competitive inhibitors of putrescine transport. Since the interaction of DESC or MESC with the polyamine transporter was strictly competitive, and because DEASC exhibits higher affinity than MESC as an inhibitor of diamine and polyamine transport, the spermine head and the cysteamine side chain of DEASC might be respectively responsible for the competitive and non-competitive components of its transport inhibition.

The biochemical properties of DESC clearly illustrate that the binding affinity of a compound can be dissociated from its ability to serve as a substrate for the polyamine transporter. The large size of DESC cannot be the main factor preventing its internalization through the channel-like portion of the transporter since MESC was also virtually impermeant. Thus, the mere attachment of an amido side chain on the spermine backbone would appear to be responsible per se for the impaired internalization of MESC and its derivatives. Indeed, $N^4$-alkylated spermidine derivatives are far better competitors of spermidine uptake than their $N^4$-acyl counterparts in mouse leukemia cells, in support of the notion that charged secondary amino groups are important in the interaction with the polyamine carrier (Porter, C. W., Cavanaugh, P. F., Jr., Stolowich, N., Ganis, B., Kelly, E., and Bergeron, R. J. 1985. *Cancer Res.* 45:2050–2057). However, the latter argument cannot account for the fact that long-chain aliphatic $\alpha,\omega$-diamines with at least 6 to 7 methylene groups have an affinity comparable to that of spermidine (Lessard, M., Zhao, C., Singh, S. M. and Poulin, R. 1985. *J. Biol. Chem.* 270:1685–1694, Bergeron, R. J. and Seligsohn, H. W. 1986. *Bioinorg. Chem.* 14:345–355; Porter, C. W. and Bergeron, R. J. 1983. *Science* 219:1083–1085; Minchin, R. F., Martin, R. L., Summers, L. A., and Ilett, K. F. 1989. *Biochem. J.* 262:391–395; Gordonsmith, R. H., Brooke-Taylor, S., Smith, L. L. and Cohen, G. M. 1983. *Biochem. Pharmacol.* 32:3701–3709). A more likely explanation for the poor affinity of polyamines bearing an acyl side chain might be the steric hindrance due to the amide group, which restricts the freedom of rotation around the adjacent carbon and nitrogen atoms. There are indications that cyclic or pseudocyclic conformations of polyamines stabilized by hydrogen bonds might be energetically favored for recognition and/or internalization of substrates of the polyamine transport system (Lessard, M., Zhao, C., Singh, S. M. and Poulin R. 1995. *J. Biol. Chem.* 270:1685–1694; Bergeron, R. J. and Seligsohn, H. W. 1986. *Bioinorg, Chem,* 14:345–355). The formation of such folded conformers would be impaired by the presence of an amide group next to the polyamine chain. In support of this hypothesis, chlorambucil-spermidine, which bears a N-propyl chlorambucil carboxamide side chain on the central nitrogen of spermidine, is a good substrate of the polyamine transport system, with a $K_m$ averaging that of spermidine (Holley, J. L., Mather, A., Wheelhouse, R. T., Cullis, P. M., Hartley, J. A., Bingham, J. P., and Cohen, G. M. 1992. *Cancer Res.* 52:4190–4195). In marked contrast, a spermidine conjugate with a chlorambucil carboxamide side chain directly attached at the c5 position of the spermidine head is a very poor substrate of the polyamine uptake system (Stark, P. A., Thrall, B. D., Meadows, G. G., and Abdel-Monem, M. M. 1992. *J. Med. Chem.* 35:4264–4269).

Although a 40-fold molar excess of DESC dramatically reduced the rate of spermidine uptake in ZR-75-1 cells, slow but continuous spermidine accumulation was still observed in the presence of the inhibitor. The low rate of polyamine internalization observed even in the presence of a large excess of DESC, in addition to the slow decomposition of the inhibitor, may largely explain the complete inability of DESC to prevent polyamine-mediated prevention of growth inhibition by DFMO.

Since the affinity of MESC thioethers remains virtually unaffected relative to the unconjugated polyamine, MESC-ASIB might serve as a photoaffinity label to detect polyamine-binding proteins, including the polyamine carrier. Experiments are currently conducted with $^{125}I$ labeled MESC-ASIB to assess its usefulness as a probe to identify the mammalian polyamine transporter. A recent report has described the specific labeling of discrete plasma membrane proteins using $^{125}I$-labeled $N^1$-azidosalicylamido-norspermine and $N^4$-azidosalicylamidoethylspermidine as photoaffinity reagents (Felschow, D. M., MacDiarmid, J., Bardos, T., Wu, R., Woster, P. M. and Porter, C. W. 1995. *J. Biol. Chem.* 270:28705–28711). However, these conjugates are internalized by mammalian cells (Felschow, D. M., MacDiarmid, J., Bardos, T., Wu, R., Woster, P. M. and Porter, C. W. 1995. *J. Biol. Chem.* 270:28705–28711), and MESC-ASIB or similar derivatives could be useful as a photoactivatable probes to exclude labeling of intracellular proteins.

The slow degradation of DESC observed in growth media, but not in PBS, was likely to L-cystine, which is present at 100 and 200 $\mu$M in IMEM or RPMI 1640 medium, respectively, through the formation of mixed disulfides with DESC. Nevertheless, the cytotoxicity of high concentrations of DESC and MESC is unlikely to be solely due to the formation of such adducts, since MESC was less toxic that DESC, despite the fact that the free thiol group of the former would make it more reactive L-cystine]. The present data clearly show that DESC has remarkably low toxicity in comparison with its homolog spermine. Thus, the basic features of this molecule, including its resistance to BSAO, should be useful for the design of potent transport inhibitors with minor non-specific effects on cell viability. The inherent structural features of DESC that confer its high affinity and resistance to uptake should thus provide a useful framework for the design of potent irreversible inhibitors of polyamine transport, which could incorporate an alkylating group such as that used in the design of specific sulcide substrates of mammalian glucose transporters (Clark, A. E., and Holman, G. D. 1990. *Biochem. J.* 269:615–622; Lehmann, J., and Scheuring, M. 1995. *Carbohydrate Res.* 276:57–74)].

CONCLUSION

For easiness of construction, polyamine derivatives (natural or synthetic) comprising sulfur in the side chain have been made, because they conducted to the formation of dimers simply by forming a disulfide bridge. Interestingly, by-products which are not dimers have also shown an activity. However, it will be readily apparent to those skilled in the art that compounds being more stable than those containing sulfur atoms are contemplated. Therefore, the side chains used for increasing the affinity of the derivatives for a polyamine transporter and/or as substrates for labelling molecules and/or as a spacer in the making of a dimer can be varied to optimize the characteristics of the derivatives of the present invention. Any equivalent structures or modifications obtainable without departing from the teachings and the spirit of this invention are considered as part of the scope thereof because the invention is in no way limited to the particularly disclosed embodiments, as reflected in the appended claims.

What is claimed is:

1. A synthetic derivative of a dimer of an original polyamine, wherein the original polyamine is modified to comprise an amido group immediately linked to a carbon atom of said original polyamine and being located between two internal atoms, said dimer being linked together by a sparer side chain anchored to the amido group of each monomer.

2. A synthetic derivative according to claim 1, wherein said synthetic derivative is capable of inhibiting the cellular uptake of a natural polyamine by specifically binding a cellular transporter for said natural polyamine.

3. A synthetic derivative according to claim 2 wherein the original polyamine comprises putrescine, spermidine and spermine.

4. A synthetic derivative according to claim 3, wherein the original polyamine is selected from the group consisting of putrescine, spermidine and spermine.

5. A synthetic derivative according to claim 4, wherein the original polyamine is spermine.

6. A synthetic derivative according to claim 2, wherein said synthetic derivative has the following general formula:

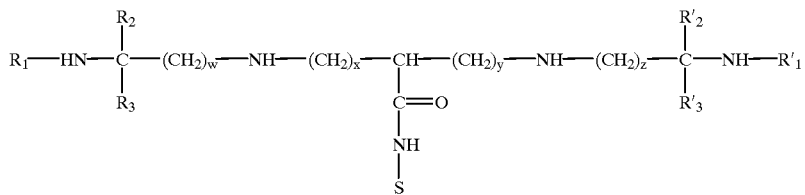

in which $R_1$ and $R'_1$ independently represent a hydrogen atom or an alkyl group having 1 to 2 carbon atoms, $R_2$, $R'_2$, $R_3$ and $R'_3$ independently represent a hydrogen atom or a methyl group, w and z independently represent an integer of 2 or 3, x represents an integer from 0 to n, n represents an integer from 3 to 6, the sum of x and y equals n, and S represents a hydrogen atom or a molecule which cannot be captured by said natural polyamine transporter.

7. A synthetic derivative according to claim 3, wherein said monomer has the following general formula:

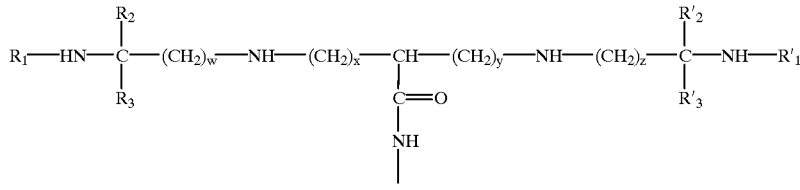

in which $R_1$ and $R'_1$ independently represent a hydrogen atom or an alkyl group having 1 to 2 carbon atoms, $R_2$, $R'_2$, $R_3$ and $R'_3$ independently represent a hydrogen atom or a methyl group, w and z independently represent an integer of 2 or 3, x represents an integer from 0 to n, n represents an integer from 3 to 6, the sum of x and y equals n, and wherein the spacer side chain comprises a linear hydrocarbon-containing backbone of 3 to 8 atoms.

8. A derivative according to claim 7, wherein said backbone comprises sulfur, oxygen or nitrogen.

9. A derivative according to claim 6, wherein w=2, z=2, x=0 and y=3.

10. A derivative according to claim 7, wherein w=2, z=2, x=0 and y=3.

11. A derivative according to claim 8, where w=2, z=2, x=0 and y=3.

12. A derivative according to claim 11, wherein the hydrocarbon-containing backbone comprises a disulfide bridge.

13. A derivative according to claim 9, which is N(2-mercaptoethyl)spermine-5-carboxamide.

14. A derivative according to claim 9, which is N(2,2'-dithio(ethyl, 1'-aminoethyl)spermine-5-carboxamide.

15. A derivative according to claim 12 which is 2,2'-dithiobis(N-ethylspermine-5-carboxamide).

16. A method for inhibiting the activity of a natural polyamine transporter comprising the step of contacting said transporter with an inhibitorily effective amount of the synthetic derivative of claim 1.

17. A method for marking a polyamine transporter comprising the steps of labeling the synthetic derivative of claim 1 with a labelling molecule to provide a labelled synthetic derivative, binding said labelled synthetic derivative to a polyamine transporter and detecting bound labelled synthetic derivative as a marker of polyamine transporter.

18. A pharmaceutical composition comprising a synthetic derivative according to claim 1 in adjunction with an acceptable pharmaceutical carrier.

19. The pharmaceutical composition of claim 18, further comprising an inhibitor of polyamine synthesis.

20. The pharmaceutical composition of claim 19, wherein said inhibitor of polyamine synthesis is α-difluoromethylornithine.

21. The method of claim 16, wherein the synthetic derivative is administered in combination with an inhibitor of polyamine synthesis.

22. The method of claim 21, wherein the inhibitor of polyamine synthesis is DFMO.

23. The method of claim 16 wherein presence of bound labelled synthetic derivative is diagnostic of a disorder involving unrestrained cell proliferation or differentiation where control of polyamine transport is required.

* * * * *

UNITED STATES PATENT AND TRADEMARK OFFICE
CERTIFICATE OF CORRECTION

PATENT NO. : 6,083,496
DATED : July 4, 2000
INVENTOR(S) : Richard Poulin et al.

It is certified that error appears in the above-identified patent and that said Letters Patent is hereby corrected as shown below:

Page 2, "Other Publications, please add -- Huber et al., *J. Biol. Chem.*, 271(44), 27556-27563, 1996. --

Column 22,
Line 3, please remove "6" and insert therefor -- 8 --.

Signed and Sealed this

Twenty-first Day of August, 2001

Attest:

NICHOLAS P. GODICI
Attesting Officer     Acting Director of the United States Patent and Trademark Office